US008481268B2

(12) United States Patent
Chee et al.

(10) Patent No.: US 8,481,268 B2
(45) Date of Patent: *Jul. 9, 2013

(54) USE OF MICROFLUIDIC SYSTEMS IN THE DETECTION OF TARGET ANALYTES USING MICROSPHERE ARRAYS

(75) Inventors: Mark S. Chee, Encinitas, CA (US); Todd A. Dickinson, San Diego, CA (US); Kevin Gunderson, Encinitas, CA (US); Don O'Neil, San Juan Capistrano, CA (US); John R. Stuelpnagel, Encinitas, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/299,235

(22) Filed: Nov. 17, 2011

(65) Prior Publication Data

US 2012/0129716 A1    May 24, 2012

Related U.S. Application Data

(63) Continuation of application No. 10/897,899, filed on Jul. 23, 2004, now Pat. No. 8,080,380, which is a continuation-in-part of application No. 09/990,890, filed on Nov. 21, 2001, now abandoned, said application No. 10/897,899 is a continuation-in-part of application No. 09/979,236, filed as application No. PCT/US00/13942 on May 22, 2000, now abandoned, which is a continuation-in-part of application No. 09/316,154, filed on May 21, 1999, now abandoned.

(60) Provisional application No. 60/252,227, filed on Nov. 21, 2000.

(51) Int. Cl.
*C12Q 1/68* (2006.01)
*G01N 33/53* (2006.01)

(52) U.S. Cl.
USPC .......................................... 435/6.12; 435/7.1

(58) Field of Classification Search
None
See application file for complete search history.

(56) References Cited

U.S. PATENT DOCUMENTS

| | | | |
|---|---|---|---|
| 3,923,426 A | 12/1975 | Theeuwes |
| 4,200,110 A | 4/1980 | Peterson et al. |
| 4,499,052 A | 2/1985 | Fulwyler |
| 4,682,895 A | 7/1987 | Costello |
| 4,683,195 A | 7/1987 | Mullis et al. |
| 4,689,202 A | 8/1987 | Khoja et al. |
| 4,785,814 A | 11/1988 | Kane |
| 4,822,746 A | 4/1989 | Walt |
| 4,824,789 A | 4/1989 | Yafuso et al. |
| 4,876,187 A | 10/1989 | Duck et al. |
| 4,908,112 A | 3/1990 | Pace |
| 4,999,306 A | 3/1991 | Yafuso et al. |
| 5,002,867 A | 3/1991 | Macevicz |
| 5,011,769 A | 4/1991 | Duck et al. |
| 5,028,545 A | 7/1991 | Soini |
| 5,034,506 A | 7/1991 | Summerton et al. |
| 5,061,336 A | 10/1991 | Soane |
| 5,071,531 A | 12/1991 | Soane |
| 5,105,305 A | 4/1992 | Betzig et al. |
| 5,110,745 A | 5/1992 | Kricka et al. |
| 5,114,864 A | 5/1992 | Walt |
| 5,124,246 A | 6/1992 | Urdea et al. |
| 5,126,022 A | 6/1992 | Soane et al. |
| 5,130,238 A | 7/1992 | Malek et al. |
| 5,132,242 A | 7/1992 | Cheung |
| 5,135,627 A | 8/1992 | Soane |
| 5,143,853 A | 9/1992 | Walt |
| 5,175,270 A | 12/1992 | Nilsen et al. |
| 5,185,243 A | 2/1993 | Ullman et al. |
| 5,194,300 A | 3/1993 | Cheung |
| 5,235,033 A | 8/1993 | Summerton et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,270,163 A | 12/1993 | Gold et al. |
| 5,296,375 A | 3/1994 | Kricka et al. |
| 5,298,741 A | 3/1994 | Walt et al. |
| 5,302,509 A | 4/1994 | Cheeseman |
| 5,304,487 A | 4/1994 | Wilding et al. |
| 5,320,814 A | 6/1994 | Walt et al. |
| 5,357,590 A | 10/1994 | Auracher |
| 5,359,100 A | 10/1994 | Urdea et al. |
| 5,380,489 A | 1/1995 | Sutton et al. |
| 5,403,711 A | 4/1995 | Walder et al. |
| 5,409,818 A | 4/1995 | Davey et al. |
| 5,435,724 A | 7/1995 | Goodman et al. |
| 5,455,166 A | 10/1995 | Walker |
| 5,474,895 A | 12/1995 | Ishii et al. |
| 5,475,096 A | 12/1995 | Gold et al. |
| 5,481,629 A | 1/1996 | Tabuchi |
| 5,486,335 A | 1/1996 | Wilding et al. |
| 5,494,798 A | 2/1996 | Gerdt et al. |
| 5,494,810 A | 2/1996 | Barany et al. |
| 5,496,997 A | 3/1996 | Pope |
| 5,498,392 A | 3/1996 | Wilding et al. |
| 5,512,490 A | 4/1996 | Walt et al. |
| 5,516,635 A | 5/1996 | Ekins et al. |

(Continued)

FOREIGN PATENT DOCUMENTS

| EP | 0269764 A1 | 6/1988 |
|---|---|---|
| EP | 0478319 A1 | 4/1992 |

(Continued)

OTHER PUBLICATIONS

Abel et al., "Fiber-Optic Evanescent Wave Biosensor for the Detection of Oligonucleotides," Anal. Chem. 68:2905-2912(1996).

(Continued)

*Primary Examiner* — Prabha Chunduru
(74) *Attorney, Agent, or Firm* — Knobbe, Martens, Olson & Bear, LLP

(57) ABSTRACT

The invention relates generally to methods and apparatus for conducting analyses, particularly microfluidic devices for the detection of target analytes.

48 Claims, 4 Drawing Sheets

U.S. PATENT DOCUMENTS

| | | | |
|---|---|---|---|
| 5,518,883 A | 5/1996 | Soini | |
| 5,541,311 A | 7/1996 | Dahlberg et al. | |
| 5,545,730 A | 8/1996 | Urdea et al. | |
| 5,565,324 A | 10/1996 | Still et al. | |
| 5,567,588 A | 10/1996 | Gold et al. | |
| 5,569,364 A | 10/1996 | Hooper et al. | |
| 5,571,670 A | 11/1996 | Urdea et al. | |
| 5,573,907 A | 11/1996 | Carrino et al. | |
| 5,573,909 A | 11/1996 | Singer et al. | |
| 5,575,849 A | 11/1996 | Honda et al. | |
| 5,580,731 A | 12/1996 | Chang et al. | |
| 5,585,069 A | 12/1996 | Zanzucchi et al. | |
| 5,587,128 A | 12/1996 | Wilding et al. | |
| 5,591,584 A | 1/1997 | Chang et al. | |
| 5,593,838 A | 1/1997 | Zanzucchi et al. | |
| 5,594,117 A | 1/1997 | Urdea et al. | |
| 5,594,118 A | 1/1997 | Urdea et al. | |
| 5,595,877 A | 1/1997 | Gold et al. | |
| 5,597,909 A | 1/1997 | Urdea et al. | |
| 5,603,351 A | 2/1997 | Cherukuri et al. | |
| 5,604,097 A | 2/1997 | Brenner | |
| 5,614,402 A | 3/1997 | Dahlberg et al. | |
| 5,616,464 A | 4/1997 | Albagli et al. | |
| 5,624,802 A | 4/1997 | Urdea et al. | |
| 5,631,337 A | 5/1997 | Sassi et al. | |
| 5,632,876 A | 5/1997 | Zanzucchi et al. | |
| 5,632,957 A | 5/1997 | Heller et al. | |
| 5,633,972 A | 5/1997 | Walt et al. | |
| 5,635,352 A | 6/1997 | Urdea et al. | |
| 5,635,358 A | 6/1997 | Wilding et al. | |
| 5,637,459 A | 6/1997 | Burke et al. | |
| 5,637,469 A | 6/1997 | Wilding et al. | |
| 5,639,603 A | 6/1997 | Dower et al. | |
| 5,643,738 A | 7/1997 | Zanzucchi et al. | |
| 5,656,241 A | 8/1997 | Seifert et al. | |
| 5,660,988 A | 8/1997 | Duck et al. | |
| 5,679,524 A | 10/1997 | Nikiforov et al. | |
| 5,681,484 A | 10/1997 | Zanzucchi et al. | |
| 5,681,697 A | 10/1997 | Urdea et al. | |
| 5,681,702 A | 10/1997 | Collins et al. | |
| 5,683,867 A | 11/1997 | Biesecker et al. | |
| 5,690,894 A | 11/1997 | Pinkel et al. | |
| 5,705,337 A | 1/1998 | Gold et al. | |
| 5,719,028 A | 2/1998 | Dahlberg et al. | |
| 5,726,026 A | 3/1998 | Wilding et al. | |
| 5,747,169 A | 5/1998 | Fan et al. | |
| 5,750,015 A | 5/1998 | Soane et al. | |
| 5,755,942 A | 5/1998 | Zanzucchi et al. | |
| 5,763,175 A | 6/1998 | Brenner | |
| 5,767,259 A | 6/1998 | Albagli et al. | |
| 5,770,029 A | 6/1998 | Nelson et al. | |
| 5,780,231 A | 7/1998 | Brenner | |
| 5,795,453 A | 8/1998 | Gilmartin | |
| 5,795,493 A | 8/1998 | Bukhman et al. | |
| 5,795,714 A | 8/1998 | Cantor et al. | |
| 5,814,524 A | 9/1998 | Walt | |
| 5,830,711 A | 11/1998 | Barany et al. | |
| 5,840,256 A | 11/1998 | Demers et al. | |
| 5,843,669 A | 12/1998 | Kaiser et al. | |
| 5,846,717 A | 12/1998 | Brow et al. | |
| 5,854,684 A | 12/1998 | Stabile et al. | |
| 5,856,083 A | 1/1999 | Chelsky et al. | |
| 5,858,195 A | 1/1999 | Ramsey | |
| 5,858,732 A | 1/1999 | Solomon et al. | |
| 5,861,697 A | 1/1999 | Sugita et al. | |
| 5,863,708 A | 1/1999 | Zanzucchi et al. | |
| 5,888,723 A | 3/1999 | Sutton et al. | |
| 5,900,481 A | 5/1999 | Lough et al. | |
| 6,013,456 A | 1/2000 | Akhavan-Tafti | |
| 6,023,540 A | 2/2000 | Walt et al. | |
| 6,027,889 A | 2/2000 | Barany et al. | |
| 6,051,380 A | 4/2000 | Sosnowski et al. | |
| 6,054,564 A | 4/2000 | Barany et al. | |
| 6,063,573 A | 5/2000 | Kayyem | |
| 6,083,763 A | 7/2000 | Balch | |
| 6,096,496 A | 8/2000 | Frankel | |
| 6,110,678 A | 8/2000 | Weisburg et al. | |
| 6,168,948 B1 | 1/2001 | Anderson et al. | |
| 6,172,218 B1 | 1/2001 | Brenner | |
| 6,200,737 B1 | 3/2001 | Walt et al. | |
| 6,210,910 B1 | 4/2001 | Walt et al. | |
| 6,251,639 B1 | 6/2001 | Kurn | |
| 6,266,459 B1 | 7/2001 | Walt et al. | |
| 6,268,148 B1 | 7/2001 | Barany et al. | |
| 6,274,323 B1 | 8/2001 | Bruchez et al. | |
| 6,284,465 B1 | 9/2001 | Wolber | |
| 6,323,042 B1 | 11/2001 | Narang et al. | |
| 6,327,410 B1 | 12/2001 | Walt et al. | |
| 6,377,721 B1 | 4/2002 | Walt et al. | |
| 6,406,845 B1 | 6/2002 | Walt et al. | |
| 6,482,593 B2 | 11/2002 | Walt et al. | |
| 6,544,732 B1 | 4/2003 | Chee et al. | |
| 6,613,211 B1 | 9/2003 | McCormick et al. | |
| 6,632,655 B1 * | 10/2003 | Mehta et al. | 506/14 |
| 6,667,159 B1 | 12/2003 | Walt et al. | |
| 6,859,570 B2 | 2/2005 | Walt et al. | |
| 6,942,771 B1 | 9/2005 | Kayyem | |
| 7,115,884 B1 | 10/2006 | Walt et al. | |
| 7,348,181 B2 | 3/2008 | Walt et al. | |
| 8,080,380 B2 * | 12/2011 | Chee et al. | 435/6.12 |
| 2001/0029049 A1 | 10/2001 | Walt et al. | |
| 2002/0051971 A1 | 5/2002 | Stuelphagel et al. | |
| 2002/0122612 A1 | 9/2002 | Walt et al. | |
| 2002/0132221 A1 | 9/2002 | Chee et al. | |
| 2003/0027126 A1 | 2/2003 | Walt et al. | |
| 2005/0233318 A1 | 10/2005 | Chee et al. | |

FOREIGN PATENT DOCUMENTS

| | | |
|---|---|---|
| EP | 0320308 B1 | 11/1993 |
| EP | 0336731 B1 | 5/1994 |
| EP | 0439182 B1 | 4/1996 |
| EP | 0637998 B1 | 7/1996 |
| EP | 0723146 A1 | 7/1996 |
| EP | 0637996 B1 | 7/1997 |
| WO | WO 89/09835 | 10/1989 |
| WO | WO 89/11101 A1 | 11/1989 |
| WO | WO 89/12696 | 12/1989 |
| WO | WO 90/01069 | 2/1990 |
| WO | WO 93/02360 A1 | 2/1993 |
| WO | WO 93/25563 A1 | 12/1993 |
| WO | WO 94/02515 | 2/1994 |
| WO | WO 95/00666 | 1/1995 |
| WO | WO 95/00667 | 1/1995 |
| WO | WO 95/05480 | 2/1995 |
| WO | WO 95/14106 | 5/1995 |
| WO | WO 95/16918 | 6/1995 |
| WO | WO 96/03212 A1 | 2/1996 |
| WO | WO 96/04547 | 2/1996 |
| WO | WO 96/15450 | 5/1996 |
| WO | WO 96/15576 | 5/1996 |
| WO | WO 96/30392 A1 | 10/1996 |
| WO | WO 96/39252 | 12/1996 |
| WO | WO 96/39260 | 12/1996 |
| WO | WO 97/05480 | 2/1997 |
| WO | WO 97/07880 | 3/1997 |
| WO | WO 97/14028 A2 | 4/1997 |
| WO | WO 97/14928 | 4/1997 |
| WO | WO 97/16561 | 5/1997 |
| WO | WO 97/16835 | 5/1997 |
| WO | WO 97/20014 | 6/1997 |
| WO | WO 97/27324 | 7/1997 |
| WO | WO 97/31256 A3 | 8/1997 |
| WO | WO 97/37755 | 10/1997 |
| WO | WO 97/40385 A1 | 10/1997 |
| WO | WO 97/43629 | 11/1997 |
| WO | WO 97/46704 A1 | 12/1997 |
| WO | WO 98/13523 A1 | 4/1998 |
| WO | WO 98/13683 | 4/1998 |
| WO | WO 98/20162 A2 | 5/1998 |
| WO | WO 98/31836 A1 | 7/1998 |
| WO | WO 98/40385 A1 | 9/1998 |
| WO | WO 98/40726 A1 | 9/1998 |
| WO | WO 98/46797 | 10/1998 |
| WO | WO 98/50782 A3 | 11/1998 |
| WO | WO 98/53093 A1 | 11/1998 |
| WO | WO 98/53300 A2 | 11/1998 |
| WO | WO 99/18434 A1 | 4/1999 |

| | | |
|---|---|---|
| WO | WO 99/39001 | 8/1999 |
| WO | WO 99/45357 A2 | 9/1999 |
| WO | WO 99/60170 A1 | 11/1999 |
| WO | WO 99/64867 A1 | 12/1999 |
| WO | WO 99/67414 | 12/1999 |
| WO | WO 99/67641 | 12/1999 |
| WO | WO 00/04372 A1 | 1/2000 |
| WO | WO 00/13004 A2 | 3/2000 |
| WO | WO 00/16101 | 3/2000 |
| WO | WO 00/16101 A2 | 3/2000 |
| WO | WO 00/39587 | 7/2000 |
| WO | WO 00/47996 | 8/2000 |
| WO | WO 00/48000 | 9/2000 |
| WO | WO 00/58516 A2 | 10/2000 |
| WO | WO 00/63437 | 10/2000 |
| WO | WO 00/71243 | 11/2000 |
| WO | WO 00/71992 A1 | 11/2000 |
| WO | WO 00/71995 | 11/2000 |
| WO | WO 00/75373 | 12/2000 |

OTHER PUBLICATIONS

Anonymous, "Fluorescent Microspheres," Tech. Note 19, Bangs Laboratories, (Fishers, In) Feb. 1997.

Anonymous,"Microsphere Selection Guide," Bangs Laboratories, (Fishers, In) Sep. 1998.

Bangs, L.B. "Immunological Applications of Microspheres," The Latex Course, Bangs Laboratories (Carmel, IN) Apr. 1996.

Barnard et al., "A Fiber-Optic Chemical Sensor with Discrete Sensing Sites," Nature, 353:338-340 (Sep. 1991).

Czarnik, "Illuminating the SNP genomic code," Modern Drug Discovery, 1(2):49-55 (1998).

Drmanac, R. et al., " Sequencing by Oligonucleotide Hybridization: A Promising Framework in Decoding of the Genome Program," The First International Conference on Electrophoresis, Supercomputing and the Human Genome, Proceeding of the Apr. 10-13, 1990 Conference at Florida State University. Ed. C. Cantor and H. Lim.

Drmanac, R. et al., "Prospects for a Miniaturized, Simplified and Frugal Human Genome Project," Scientia Yugoslavica, 16(1-2):97-107 (1990).

Drmanac, R. et al., "Sequencing by Hybridization (SBH) with Oligonucleotide Probes as an Integral Approach for the Analysis of Complex Genomes," International Journal of Genomic Research, 1(1):59-79(1992).

Drmanac, R. et al., "Sequencing by Hybridization," Automated DNA Sequencing and Analysis, ed. M. Adams, C. Fields and J. Venter. (1994).

Ferguson, et al., "A Fiber-Optic DNA Biosensor Microarray for the Analysis of Gene Expression," Nature Biotechnology, 14:1681-1684 (1996).

Fuh et al., "Single Fiber-Optic Fluorescence pH Probe," Analyst, 112:1159-1163 (1987).

Grazia et al., "In-Vivo Biomedical Monitoring by Fiber-Optic Systems," Journal of Lighthwave Technology, 13(7): 1396-1406 (1995).

Healey et al., "Development of a Penicillin Biosensor Using a Single Optic Imaging Fiber," SPIE Proc. 2388:568-573 (1995).

Healey et al., "Improved Fiber-Optic Chemical Sensor for Penicillin," Anal.Chem. 67(24):4471-4476 (1995).

Healy et al., "Fiberoptic DNA Sensor Array Capable of Detecting Point Mutations," Analytical Biochemistry, 251:270-279(1997).

Hirschfeld et al., "Laser-Fiber-Optic 'Optrode' for Real Time In Vivo Blood Carbon Dioxide Level Monitoring," Journal of Lightwave Technology, LT-5(7):1027-1033 (1987).

Lyamichev et al. "Polymorphism identification and quantitative detection of genomic DNA by invasive cleavage of oligonucleotide probes," Nature Biotechnology, 17:292-296 (1999). (added Apr. 3, 2001 892 68087-2).

Magnani et al., "In-Vivo Biomedical Monitoring by Fiber-Optic Systems." Journal of Lightwave Technology, 13(7):1396-1406 (1995).

Michael et al. "Fabrication of Micro-and Nanostructures Using Optical Imaging Fibers and there Use as Chemical Sensors," Proc. $3^{rd}$ Intl. Symp. Microstructures and Microfabricated Systems, ed. P.J. Hesketh, et al., v. 97-5, Electrochem. Soc., 152-157 (Aug. 1997).

Michael et al., "Making Sensors out of Disarray: Optical Sensor Microarrays," Proc. SPIE, 3270:34-41 (1998).

Michael et al., "Randomly Ordered Addressable High-Density Optical Sensor Arrays," Anal. Chem. 70(7): 1241-1248 (Apr. 1998).

Pantano et al., "Ordered Nanowell Arrays," Chem Mater., 8(12):2832-2835 (1996).

Peterson et al., "Fiber-Optic Sensors for Biomedical Applications," Science, 13:123-127 (1984).

Peterson J. et al, "Fiber Optic pH Probe for Physiological Use," Anal. Chem., 52:864-869 (1980).

Piunno et al., "Fiber Optic DNA Sensor for Fluorometric Nucleic Acid Determination," Anal. Chem., 67:2635-2643 (1995).

Pope, E. "Fiber Optic Chemical Microsensors Employing Optically Active Silica Microspheres," SPIE, 2388:245-256 (1995).

Ronaghi et al., "A Sequencing Method Based on Real-Time Pyrophosphate," Science, 281:363-365 (1998).

Shoemaker et al., "Quantitative phenotypic analysis of yeast deletion mutants using a highly parallel molecular bar-coding strategy," Nature Genetics, 14:450-456 (1996).

Strachan et al., "A Rapid General Method for the Identification of PCR Products Using a Fiber-Optic Biosensor and its Application to the Detection of *Listeria*," Letters in Applied Microbiology, 21:5-9 (1995).

Walt "Fiber Optic Imaging Sensors," Acc. Chem. Res. 31(5):267-278 (1998).

Walt "Fiber-Optic Sensors for Continuous Clinical Monitoring," Proc. IEEE, 80(6): 903-911 (1992).

* cited by examiner

USE OF MICROFLUIDIC SYSTEMS IN THE DETECTION OF TARGET ANALYTES USING MICROSPHERE ARRAYS

This application is a continuation of U.S. application Ser. No. 10/897,899, filed Jul. 23, 2004 which is a continuation-in-part of U.S. application Ser. No. 09/990,890, filed Nov. 21, 2001, now abandoned, which claims the benefit of U.S. application Ser. No. 60/252,227, filed Nov. 21, 2000, both of which are expressly incorporated herein by reference in their entireties. U.S. application Ser. No. 10/897,899, filed Jul. 23, 2004 also is a continuation-in-part of U.S. application Ser. No. 09/979,236, filed Apr. 15, 2002, now abandoned, which is a 371 of PCT/US00/13942, filed May 22, 2000 which is a continuation-in-part of and claims priority to U.S. application Ser. No. 09/316,154, filed May 21, 1999, now abandoned. All the foregoing applications are expressly incorporated herein by reference in their entireties.

FIELD OF THE INVENTION

The invention relates generally to methods and apparatus for conducting analyses, particularly microfluidic devices for the detection of target analytes.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

One type of sensor that is showing particular promise is based on microspheres or beads that are distributed on a substrate at discrete sites. Each bead contains a chemical functionality, such as a binding partner, that can be used to detect the presence of a target analyte. The beads are put down randomly and then a variety of decoding schemes are used to elucidate the location and chemical functionality at each site. See for example PCT US98/21193, PCT US99/04473; PCT US98/05025 and PCT US98/09163.

There is a significant trend to reduce the size of these sensors, both for sensitivity and to reduce reagent costs. Thus, a number of microfluidic devices have been developed, generally comprising a solid support with microchannels, utilizing a number of different wells, pumps, reaction chambers, and the like. See for example EP 0637996 B1; EP 0637998 B1; WO96/39260; WO97/16835; WO98/13683; WO97/16561; WO97/43629; WO96/39252; WO96/15576; WO96/15450; WO97/37755; and WO97/27324; and U.S. Pat. Nos. 5,304,487; 5,071531; 5,061,336; 5,747,169; 5,296,375; 5,110,745; 5,587,128; 5,498,392; 5,643,738; 5,750,015; 5,726,026; 5,35,358; 5,126,022; 5,770,029; 5,631,337; 5,569,364; 5,135,627; 5,632,876; 5,593,838; 5,585,069; 5,637,469; 5,486,335; 5,755,942; 5,681,484; and 5,603,351.

Thus, there is a need for a microfluidic biosensor that is both small and high density, that can be used in a high throughput manner.

SUMMARY OF THE INVENTION

In accordance with the objects outlined above, the present invention provides microfluidic devices for the detection of a target analyte in a sample. The devices comprise a solid support that has any number of modules, including a sample inlet port and at least one sample handling well comprising a well inlet port and a well outlet port. The device generally further comprises a first microchannel to allow fluid contact between the sample inlet port and the sample handling well. The device also comprises a detection module comprising a substrate with a surface comprising discrete sites, and a population of microspheres comprising at least a first and a second subpopulation, wherein each subpopulation comprises a bioactive agent. The microspheres are distributed on said surface. The detection module also comprises a detection inlet port to receive the sample. The device also comprises a second microchannel to allow fluid contact between the sample handling well and the detection inlet port.

In addition the invention provides a method of assembling a detector in a microfluidic device. The method includes providing a microfluidic device comprising a first microchannel to allow fluid contact between a sample inlet port and a sample handling well, a second microchannel to allow fluid contact between said sample handling well and a detection inlet port, and a detection module comprising a substrate with a surface comprising discrete sites. The method further includes flowing a fluid across the substrate. The fluid comprises a population of microspheres comprising at least a first and a second subpopulation, wherein each subpopulation comprises a bioactive agent, whereby the beads flow across the discrete sites, and are deposited randomly in the discrete sites. The method additionally includes reversing the flow of the fluid.

In addition the invention provides a method of assembling a detector in a microfluidic device. The method includes providing a microfluidic device comprising a plurality of first micro channels, and a population of microspheres in microchannels. The device further includes a receiving chamber connected to said microchannels. The method further includes flowing said microspheres through said microchannels into said receiving chamber.

DETAILED DESCRIPTION OF THE INVENTION

Figure 1:
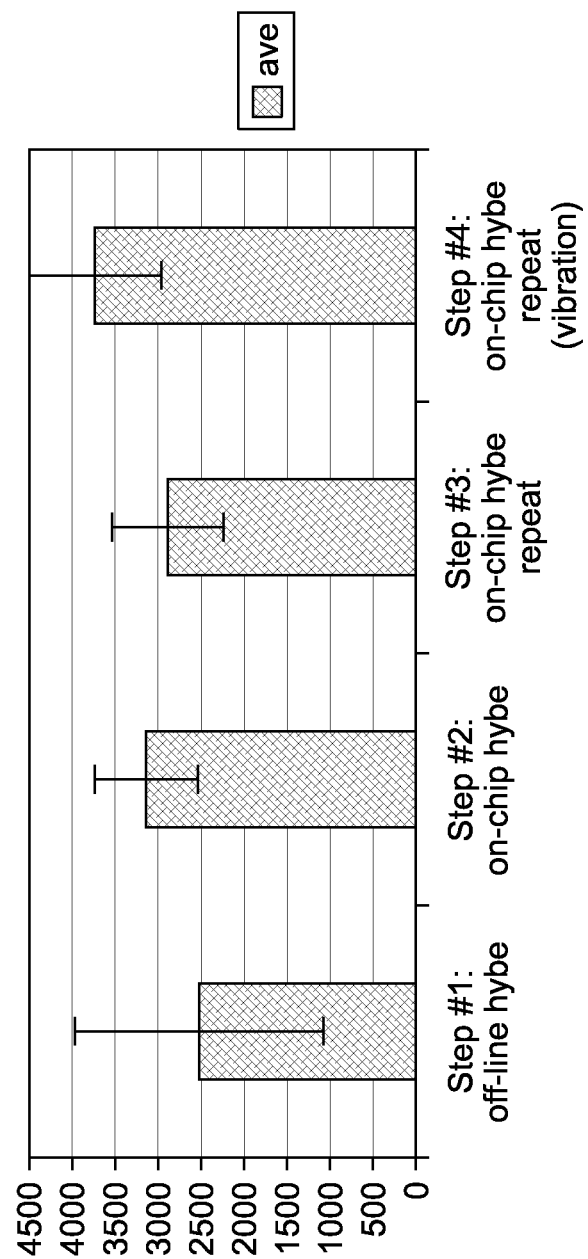
FIG. 1 graphically depicts improved signal intensity with vibration of the chip during hybridiation.

The invention provides microfluidic cassettes or devices that can be used to effect a number of manipulations on a sample to ultimately result in target analyte detection or quantification. These manipulations can include cell handling (cell concentration, cell lysis, cell removal, cell separation, etc.), separation of the desired target analyte from other sample components, chemical or enzymatic reactions on the target analyte, detection of the target analyte, etc. The devices of the invention can include one or more wells for sample manipulation, waste or reagents; microchannels to and between these wells, including microchannels containing electrophoretic separation matrices; valves to control fluid movement; on-chip pumps such as electroosmotic, electrohydrodynamic, or electrokinetic pumps; and detection systems comprising bead arrays, as is more fully described below. The devices of the invention can be configured to manipulate one or multiple samples or analytes.

The microfluidic devices of the invention are used to detect target analytes in samples. By "target analyte" or "analyte" or grammatical equivalents herein is meant any molecule, compound or particle to be detected. As outlined below, target analytes preferably bind to binding ligands, as is more fully described above. As will be appreciated by those in the art, a large number of analytes may be detected using the present methods; basically, any target analyte for which a binding ligand, described herein, may be detected using the methods of the invention.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are environmental pollutants; nucleic acids; proteins (including enzymes, antibodies, antigens, growth factors, cytokines, etc); therapeutic and abused drugs; cells; and viruses.

In a preferred embodiment, the target analyte is a nucleic acid. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644, 048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of labels or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

In a preferred embodiment, the present invention provides methods of detecting target nucleic acids. By "target nucleic acid" or "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. In some embodiments, it may be desirable to fragment or cleave the sample nucleic acid into fragments of 20 to 10,000 basepairs, with fragments of roughly 500 basepairs being preferred in some embodiments. For hybridization purposes, smaller fragments are generally preferred. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others.

As is outlined more fully below, probes (including primers) are made to hybridize to target sequences to determine the presence or absence of the target sequence in a sample. Generally speaking, this term will be understood by those skilled in the art.

The target sequence may also be comprised of different target domains, for example, in "sandwich" type assays as outlined below, a first target domain of the sample target sequence may hybridize to a capture probe or capture extender probe and a second target domain may hybridize to a portion of an amplifier probe, a label probe, or a different capture or capture extender probe, etc. In addition, the target domains may be adjacent (i.e. contiguous) or separated. For example, when ligation techniques are used, a first primer may hybridize to a first target domain and a second primer may hybridize to a second target domain; either the domains are adjacent, or they may be separated by one or more nucleotides, coupled with the use of a polymerase and dNTPs, as is more fully outlined below.

The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

In a preferred embodiment, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. As discussed below, when the protein is used as a binding ligand, it may be desirable to utilize protein analogs to retard degradation by sample contaminants.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

These target analytes may be present in any number of different sample types, including, but not limited to, bodily fluids including blood, lymph, saliva, vaginal and anal secretions, urine, feces, perspiration and tears, and solid tissues, including liver, spleen, bone marrow, lung, muscle, brain, etc.

Accordingly, the present invention provides microfluidic devices for the detection of target analytes comprising a solid substrate. As outlined below, the substrate making up the microfluidic device (generally referred to herein as the "device substrate") may be the same or different from the substrate of the detection array (generally referred to herein as the "array substrate", defined below). The solid substrate can be made of a wide variety of materials and can be configured in a large number of ways, as is discussed herein and will be apparent to one of skill in the art. In addition, a single device may comprise more than one substrate; for example, there may be a "sample treatment" cassette that interfaces with a separate "detection" cassette; a raw sample is added to the sample treatment cassette and is manipulated to prepare the sample for detection, which is removed from the sample treatment cassette and added to the detection cassette. There may be an additional functional cassette into which the device fits; for example, a heating element which is placed in contact with the sample cassette to effect reactions such as PCR. In some cases, a portion of the substrate may be removable; for example, the sample cassette may have a detachable detection cassette, such that the entire sample cassette is not contacted with the detection apparatus. See for example U.S. Pat. No. 5,603,351 and PCT US96/17116, hereby incorporated by reference.

The composition of the device substrate will depend on a variety of factors, including the techniques used to create the device, the use of the device, the composition of the sample, the analyte to be detected, the size of the wells and microchannels, the presence or absence of electronic components, etc. Generally, the devices of the invention should be easily sterilizable, exhibit low fluorescence and non-specific binding, be biocompatible and resist temperature changes.

In a preferred embodiment, the microfluidic solid substrate can be made from a wide variety of materials, including, but not limited to, silicon such as silicon wafers, silicon dioxide, silicon nitride, glass and fused silica, gallium arsenide, indium phosphide, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, superalloys, zircaloy, steel, gold, silver, copper, tungsten, molybdeum, tantalum, KOVAR, KEVLAR, KAPTON, MYLAR, brass, sapphire, etc. High quality glasses such as high melting borosilicate or fused silicas may be preferred for their UV transmission properties when any of the sample manipulation steps require light based technologies. In addition, as outlined herein, portions of the internal surfaces of the device may be coated with a variety of coatings as needed, to reduce non-specific binding, to allow the attachment of binding ligands, etc.

The devices of the invention can be made in a variety of ways, as will be appreciated by those in the art. See for example WO96/39260, directed to the formation of fluid-tight electrical conduits; U.S. Pat. No. 5,747,169, directed to sealing; and EP 0637996 B 1; EP 0637998 B 1; WO96/39260; WO97/16835; WO98/13683; WO97/16561; WO97/43629; WO96/39252; WO96/15576; WO96/15450; WO97/37755; and WO97/27324; and U.S. Pat. Nos. 5,304,487; 5,071531; 5,061,336; 5,747,169; 5,296,375; 5,110,745; 5,587,128; 5,498,392; 5,643,738; 5,750,015; 5,726,026; 5,35,358; 5,126,022; 5,770,029; 5,631,337; 5,569,364; 5,135,627; 5,632,876; 5,593,838; 5,585,069; 5,637,469; 5,486,335; 5,755,942; 5,681,484; and 5,603,351, all of which are hereby incorporated by reference. Suitable fabrication techniques again will depend on the choice of substrate, but preferred methods include, but are not limited to, a variety of micromachining and microfabrication techniques, including film deposition processes such as spin coating, chemical vapor deposition, laser fabrication, photolithographic and other etching techniques using either wet chemical processes or plasma processes, embossing, injection molding, and bonding techniques (see U.S. Pat. No. 5,747,169, hereby incorporated by reference). In addition, there are printing techniques for the creation of desired fluid guiding pathways; that is, patterns of printed material can permit directional fluid transport. Thus, the build-up of "ink" can serve to define a flow channel. In addition, the use of different "inks" or "pastes" can allow different portions of the pathways having different flow properties. For example, materials can be used to change solute/solvent RF values (the ratio of the distance moved by a particular solute to that moved by a solvent front). For example, printed fluid guiding pathways can be manufactured with a printed layer or layers comprised of two different materials, providing different rates of fluid transport. Multi-material fluid guiding pathways can be used when it is desirable to modify retention times of reagents in fluid guiding pathways. Furthermore, printed fluid guiding pathways can also provide regions containing reagent substances, by including the reagents in the "inks" or by a subsequent printing step. See for example U.S. Pat. No. 5,795,453, herein incorporated by reference in its entirety.

In a preferred embodiment, the solid substrate is configured for handling a single sample that may contain a plurality of target analytes. That is, a single sample is added to the device and the sample may either be aliquoted for parallel processing for detection of the analytes or the sample may be processed serially, with individual targets being detected in a serial fashion.

In a preferred embodiment, the solid substrate is configured for handling multiple samples, each of which may contain one or more target analytes. In general, in this embodiment, each sample is handled individually; that is, the manipulations and analyses are done in parallel, with preferably no contact or contamination between them. Alternatively, there may be some steps in common; for example, it may be desirable to process different samples separately but detect all of the target analytes on a single detection array, as described below.

In addition, it should be understood that while most of the discussion herein is directed to the use of planar substrates with microchannels and wells, other geometries can be used as well. For example, two or more planar substrates can be stacked to produce a three dimensional device, that can contain microchannels flowing within one plane or between planes; similarly, wells may span two or more substrates to allow for larger sample volumes. Thus for example, both sides of a substrate can be etched to contain microchannels; see for example U.S. Pat. Nos. 5,603,351 and 5,681,484, both of which are hereby incorporated by reference.

Thus, the devices of the invention include at least one microchannel or flow channel that allows the flow of sample from the sample inlet port to the other components or modules of the system. The collection of microchannels and wells is sometimes referred to in the art as a "mesoscale flow system". As will be appreciated by those in the art, the flow channels may be configured in a wide variety of ways, depending on the use of the channel. For example, a single flow channel starting at the sample inlet port may be separated into a variety of smaller channels, such that the original sample is divided into discrete subsamples for parallel processing or analysis. Alternatively, several flow channels from different modules, for example the sample inlet port and a reagent storage module may feed together into a mixing chamber or a reaction chamber. As will be appreciated by those in the art, there are a large number of possible configurations; what is important is that the flow channels allow the movement of sample and reagents from one part of the device to another. For example, the path lengths of the flow channels may be altered as needed; for example, when mixing and timed reactions are required, longer and sometimes tortuous flow channels can be used; similarly, longer lengths for separation purposes may also be desirable. Alternatively, the size of a channel may be changed to increase or reduce the flow rate of the sample. For example, the size of a channel may be increased in order to reduce sample flow rate.

In general, the microfluidic devices of the invention are generally referred to as "mesoscale" devices. The devices herein are typically designed on a scale suitable to analyze microvolumes, although in some embodiments large samples (e.g. cc's of sample) may be reduced in the device to a small volume for subsequent analysis. That is, "mesoscale" as used herein refers to chambers and microchannels that have cross-sectional dimensions on the order of 0.1 µm to 500 µm. The mesoscale flow channels and wells have preferred depths on the order of 0.1 µm to 100 µm, typically 2-50 µm. The channels have preferred widths on the order of 2.0 to 500 µm, more preferably 3-100 µm. For many applications, channels of 5-50 µm are useful. However, for many applications, larger dimensions on the scale of millimeters may be used. Similarly, chambers (sometimes also referred to herein as "wells") in the substrates often will have larger dimensions, on the scale of a few millimeters.

In addition to the flow channel system, the devices of the invention are configured to include one or more of a variety of components, herein referred to as "modules", that will be present on any given device depending on its use. These modules include, but are not limited to: sample inlet ports; sample introduction or collection modules; cell handling modules (for example, for cell lysis, cell removal, cell concentration, cell separation or capture, cell fusion, cell growth, etc.); separation modules, for example, for electrophoresis, gel filtration, sedimentation, etc.); reaction modules for chemical or biological alteration of the sample, including amplification of the target analyte (for example, when the target analyte is nucleic acid, amplification techniques are useful, including, but not limited to polymerase chain reaction (PCR), ligase chain reaction (LCR), strand displacement amplification (SDA), and nucleic acid sequence based amplification (NASBA)), chemical, physical or enzymatic cleavage or alteration of the target analyte, or chemical modification of the target; fluid pumps; fluid valves; heating modules; storage modules for assay reagents; mixing chambers; and detection modules.

In a preferred embodiment, the devices of the invention include at least one sample inlet port for the introduction of the sample to the device. This may be part of or separate from a sample introduction or collection module; that is, the sample may be directly fed in from the sample inlet port to a separation chamber, or it may be pretreated in a sample collection well\ or chamber.

By port is meant a point of entry or exit, for example from a channel or well, that regulates flow of the sample. In one embodiment, the port is sealable, that is forms a seal such that the sample will not flow from sealed reservoir. The port may be a physical barrier to flow, such as a stopper or diaphragm. Alternatively, the port or barrier to flow is regulated by flow pressure, electric current and the like.

As one of ordinary skill in the art appreciates, ports may not be necessary at all points of entry or exit between the various wells and channels. However, when necessary, ports may be included at any entry or exit points. For example, in one embodiment, a sample handling well comprises a well inlet port and optionally a well outlet port. Similarly, a detection module comprises an inlet port and an outlet port.

In a preferred embodiment, the devices of the invention include a sample collection module, which can be used to concentrate or enrich the sample if required; for example, see U.S. Pat. No. 5,770,029, including the discussion of enrichment channels and enrichment means.

In a preferred embodiment, the devices of the invention include a cell handling module. This is of particular use when the sample comprises cells that either contain the target analyte or that must be removed in order to detect the target analyte. Thus, for example, the detection of particular antibodies in blood can require the removal of the blood cells for efficient analysis, or the cells must be lysed prior to detection. In this context, "cells" include viral particles that may require treatment prior to analysis, such as the release of nucleic acid from a viral particle prior to detection of target sequences. In addition, cell handling modules may also utilize a downstream means for determining the presence or absence of cells. Suitable cell handling modules include, but are not limited to, cell lysis modules, cell removal modules, cell concentration modules, and cell separation or capture modules. In addition, as for all the modules of the invention, the cell handling module is in fluid communication via a flow channel with at least one other module of the invention.

In a preferred embodiment, the cell handling module includes a cell lysis module. As is known in the art, cells may be lysed in a variety of ways, depending on the cell type. In one embodiment, as described in EP 0 637 998 B1 and U.S. Pat. No. 5,635,358, hereby incorporated by reference, the cell lysis module may comprise cell membrane piercing protrusions that extend from a surface of the cell handling module. As fluid is forced through the device, the cells are ruptured. Similarly, this may be accomplished using sharp edged particles trapped within the cell handling region. Alternatively, the cell lysis module can comprise a region of restricted cross-sectional dimension, which results in cell lysis upon pressure.

In a preferred embodiment, the cell lysis module comprises a cell lysing agent, such as detergents, NaOH, enzymes, proteinase K, guanidinium HCL, etc. In some embodiments, for example for blood cells, a simple dilution with water or buffer can result in hypotonic lysis. The lysis agent may be solution form, stored within the cell lysis module or in a storage module and pumped into the lysis module. Alternatively, the lysis agent may be in solid form, that is taken up in solution upon introduction of the sample. Temperature or mixing may also be applied.

The cell lysis module may also include, either internally or externally, a filtering module for the removal of cellular debris as needed. This filter may be microfabricated between the cell lysis module and the subsequent module to enable the removal of the lysed cell membrane and other cellular debris components; examples of suitable filters are shown in EP 0 637 998 B1, incorporated by reference.

In a preferred embodiment, the cell handling module includes a cell separation or capture module. This embodiment utilizes a cell capture region comprising binding sites capable of reversibly binding a cell surface molecule to enable the selective isolation (or removal) of a particular type of cell from the sample population. These binding moieties may be immobilized either on the surface of the module or on a particle trapped within the module (i.e. a bead) by physical absorption or by covalent attachment. Suitable binding moieties will depend on the cell type to be isolated or removed, and generally includes antibodies and other binding ligands, such as ligands for cell surface receptors, etc. Thus, a particular cell type may be removed from a sample prior to further handling, or the assay is designed to specifically bind the desired cell type, wash away the non-desirable cell types, followed by either release of the bound cells by the addition of reagents or solvents, physical removal (i.e. higher flow rates or pressures), or even in situ lysis.

Alternatively, a cellular "sieve" can be used to separate cells on the basis of size or shape. This can be done in a variety of ways, including protrusions from the surface that allow size exclusion, a series of narrowing channels, or a diafiltration type setup.

In a preferred embodiment, the cell handling module includes a cell removal module. This may be used when the sample contains cells that are not required in the assay. Generally, cell removal will be done on the basis of size exclusion as for "sieving", above, with channels exiting the cell handling module that are too small for the cells; filtration and centrifugation may also be done.

In a preferred embodiment, the cell handling module includes a cell concentration module. As will be appreciated by those in the art, this is done using "sieving" methods, for example to concentrate the cells from a large volume of sample fluid prior to lysis, or centrifugation.

In a preferred embodiment, the devices of the invention include a separation module. Separation in this context means that at least one component of the sample is separated from other components of the sample. This can comprise the separation or isolation of the target analyte, or the removal of contaminants that interfere with the analysis of the target analyte, depending on the assay.

In a preferred embodiment, the separation module includes chromatographic-type separation media such as absorptive phase materials, including, but not limited to reverse phase materials ($C_8$ or $C_{18}$ coated particles, etc.), ion-exchange materials, affinity chromatography materials such as binding ligands, etc. See U.S. Pat. No. 5,770,029.

In a preferred embodiment, the separation module utilizes binding ligands, as is generally outlined herein for cell separation or analyte detection. In this embodiment, binding ligands are immobilized (again, either by physical absorption or covalent attachment, described below) within the separation module (again, either on the internal surface of the module, on a particle such as a bead, filament or capillary trapped within the module, for example through the use of a frit). Suitable binding moieties will depend on the sample component to be isolated or removed. By "binding ligand" or grammatical equivalents herein is meant a compound that is used to bind a component of the sample, either a contaminant (for removal) or the target analyte (for enrichment). In some embodiments, as outlined below, the binding ligand is used to probe for the presence of the target analyte, and that will bind to the analyte.

As will be appreciated by those in the art, the composition of the binding ligand will depend on the sample component to be separated. Binding ligands for a wide variety of analytes are known or can be readily found using known techniques. For example, when the component is a protein, the binding ligands include proteins (particularly including antibodies or fragments thereof (FAbs, etc.)) or small molecules. When the sample component is a metal ion, the binding ligand generally comprises traditional metal ion ligands or chelators. Preferred binding ligand proteins include peptides. For example, when the component is an enzyme, suitable binding ligands include substrates and inhibitors. Antigen-antibody pairs, receptor-ligands, and carbohydrates and their binding partners are also suitable component-binding ligand pairs. The binding ligand may be nucleic acid, when nucleic acid binding proteins are the targets; alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptomers" can be developed for binding to virtually any target analyte. Similarly, there is a wide body of literature relating to the development of binding partners based on combinatorial chemistry methods. In this embodiment, when the binding ligand is a nucleic acid, preferred compositions and techniques are outlined in PCT US97/20014, hereby incorporated by reference.

In a preferred embodiment, the binding of the sample component to the binding ligand is specific, and the binding ligand is part of a binding pair. By "specifically bind" herein is meant that the ligand binds the component, for example the target analyte, with specificity sufficient to differentiate between the analyte and other components or contaminants of the test sample. The binding should be sufficient to remain bound under the conditions of the separation step or assay, including wash steps to remove non-specific binding. In some embodiments, for example in the detection of certain biomolecules, the disassociation constants of the analyte to the binding ligand will be less than about $10^{-4}$-$10^{-6}$ $M^{-1}$, with less than about $10^{-5}$ to $10^{-9}$ $M^{-1}$ being preferred and less than about $10^{4}$-$10^{-9}$ $M^{-1}$ being particularly preferred.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand is generally a substantially complementary nucleic acid. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins or small molecules. Preferred binding ligand proteins include peptides. For example, when the analyte is an enzyme, suitable binding ligands include substrates, inhibitors, and other proteins that bind the enzyme, i.e. components of a multi-enzyme (or protein) complex. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences. In a preferred embodiment, the binding ligands are portions (particularly the extracellular portions) of cell surface receptors that are known to multimerize, such as the growth hormone receptor, glucose transporters (particularly GLUT4 receptor), transferrin receptor, epidermal growth factor receptor, low density lipoprotein receptor, high density lipoprotein receptor, leptin receptor, interleukin receptors including IL-1, IL-2, IL-3, IL-4, IL-5, IL-6, IL-7, IL-8, IL-9, IL-11, IL-12, IL-13, IL-15 and IL-17 receptors, VEGF receptor, PDGF receptor, EPO receptor, TPO receptor, ciliary neurotrophic factor receptor, prolactin receptor, and T-cell receptors.

When the sample component bound by the binding ligand is the target analyte, it may be released for detection purposes if necessary, using any number of known techniques, depending on the strength of the binding interaction, including changes in pH, salt concentration, temperature, etc. or the addition of competing ligands, etc.

In a preferred embodiment, the separation module includes an electrophoresis module, as is generally described in U.S. Pat. Nos. 5,770,029; 5,126,022; 5,631,337; 5,569,364; 5,750, 015, and 5,135,627, all of which are hereby incorporated by reference. In electrophoresis, molecules are primarily separated by different electrophoretic mobilities caused by their different molecular size, shape and/or charge. Microcapillary tubes have recently been used for use in microcapillary gel electrophoresis (high performance capillary electrophoresis (HPCE)). One advantage of HPCE is that the heat resulting from the applied electric field is efficiently disippated due to the high surface area, thus allowing fast separation. The electrophoresis module serves to separate sample components by the application of an electric field, with the movement of the sample components being due either to their charge or, depending on the surface chemistry of the microchannel, bulk fluid flow as a result of electroosmotic flow (EOF).

As will be appreciated by those in the art, the electrophoresis module can take on a variety of forms, and generally comprises an electrophoretic microchannel and associated electrodes to apply an electric field to the electrophoretic microchannel. Waste fluid outlets and fluid reservoirs are present as required.

The electrodes comprise pairs of electrodes, either a single pair, or, as described in U.S. Pat. Nos. 5,126,022 and 5,750, 015, a plurality of pairs. Single pairs generally have one electrode at each end of the electrophoretic pathway. Multiple electrode pairs may be used to precisely control the movement of sample components, such that the sample components may be continuously subjected to a plurality of electric fields either simultaneously or sequentially.

In a preferred embodiment, electrophoretic gel media may also be used. By varying the pore size of the media, employing two or more gel media of different porosity, and/or providing a pore size gradient, separation of sample components can be maximized. Gel media for separation based on size are known, and include, but are not limited to, polyacrylamide and agarose. One preferred electrophoretic separation matrix is described in U.S. Pat. No. 5,135,627, hereby incorporated by reference, that describes the use of "mosaic matrix", formed by polymerizing a dispersion of microdomains ("dispersoids") and a polymeric matrix. This allows enhanced separation of target analytes, particularly nucleic acids. Similarly, U.S. Pat. No. 5,569,364, hereby incorporated by reference, describes separation media for electrophoresis comprising submicron to above-micron sized cross-linked gel particles that find use in microfluidic systems. U.S. Pat. No. 5,631,337, hereby incorporated by reference, describes the use of thermoreversible hydrogels comprising polyacrylamide backbones with N-substituents that serve to provide hydrogen bonding groups for improved electrophoretic separation. See also U.S. Pat. Nos. 5,061,336 and 5,071,531, directed to methods of casting gels in capillary tubes.

In a preferred embodiment, the devices of the invention include a reaction module. This can include either physical, chemical or biological alteration of one or more sample components. Alternatively, it may include a reaction module wherein the target analyte alters a second moiety that can then be detected; for example, if the target analyte is an enzyme, the reaction chamber may comprise a substrate that upon modification by the target analyte, can then be detected. In this embodiment, the reaction module may contain the necessary reagents, or they may be stored in a storage module and pumped as outlined herein to the reaction module as needed.

In a preferred embodiment, the reaction module includes a chamber for the chemical modification of all or part of the sample. For example, chemical cleavage of sample components (CNBr cleavage of proteins, etc.) or chemical cross-linking can be done. PCT US97/07880, hereby incorporated by reference, lists a large number of possible chemical reactions that can be done in the devices of the invention, including amide formation, acylation, alkylation, reductive amination, Mitsunobu, Diels Alder and Mannich reactions, Suzuki and Stille coupling, etc. Similarly, U.S. Pat. Nos. 5,616,464 and 5,767,259 describe a variation of ligation chain reaction (LCR; sometimes also referred to as oligonucleotide ligation amplification or OLA) that utilizes a "chemical ligation" of sorts. In this embodiment, similar to LCR, a pair of primers are utilized, wherein the first primer is substantially complementary to a first domain of the target and the second primer is substantially complementary to an adjacent second domain of the target (although, as for LCR, if a "gap" exists, a polymerase and dNTPs may be added to "fill in" the gap). Each primer has a portion that acts as a "side chain" that does not bind the target sequence and acts one half of a stem structure that interacts non-covalently through hydrogen bonding, salt bridges, van der Waal's forces, etc. Preferred embodiments utilize substantially complementary nucleic acids as the side chains. Thus, upon hybridization of the primers to the target sequence, the side chains of the primers are brought into spatial proximity, and, if the side chains comprise nucleic acids as well, can also form side chain hybridization complexes. At least one of the side chains of the primers comprises an activatable cross-linking agent, generally covalently attached to the side chain, that upon activation, results in a chemical cross-link or chemical ligation. The activatible group may comprise any moiety that will allow cross-linking of the side chains, and include groups activated chemically, photonically and thermally, with photoactivatable groups being preferred. In some embodiments a single activatable group on one of the side chains is enough to result in cross-linking via interaction to a functional group on the other side chain; in alternate embodiments, activatable groups are required on each side chain.

In a preferred embodiment, the reaction module includes a chamber for the biological alteration of all or part of the sample. For example, enzymatic processes including nucleic acid amplification and other nucleic acid modifications including ligation, cleavage, circularization, supercoiling, methylation, acetylation, sequencing, genotyping; hydrolysis of sample components or the hydrolysis of substrates by a target enzyme, the addition or removal of detectable labels, the addition or removal of phosphate groups, protein modification (acylation, glycosylation, addition of lipids, carbohydrates, etc.), the synthesis/modification of small molecules, etc. See also, U.S. Ser. No. 09/553,093 filed Apr. 20, 1999, which is expressly incorporated herein by reference.

In a preferred embodiment, the target analyte is a nucleic acid and the biological reaction chamber allows amplification of the target nucleic acid. Suitable amplification techniques include, both target amplification and probe amplification, including, but not limited to, polymerase chain reaction (PCR), ligase chain reaction (LCR), strand displacement amplification (SDA), self-sustained sequence replication (3SR), QB replicase amplification (QBR), repair chain reaction (RCR), cycling probe technology or reaction (CPT or CPR), Invader™, and nucleic acid sequence based amplification (NASBA). Techniques utilizing these methods are well known in the art and are described in more detail in U.S. Ser. Nos. 09/553,993, filed Apr. 20, 2000, 09/556,463, fled Apr. 21, 2000 and 60/244,119, filed Oct. 26, 2000, all of which are expressly incorporated herein by reference. In this embodiment, the reaction reagents generally comprise at least one enzyme (generally polymerase), primers, and nucleoside triphosphates as needed.

In a preferred embodiment the microfluidic device comprises a plurality of reaction modules. In this embodiment, the reaction modules may perform different functions. That is, for example, one reaction module performs PCR while another performs QBR. Alternatively, each reaction module performs the same function. What is important is that the reaction modules are connected to a detection module for analysis as outlined below.

General techniques for nucleic acid amplification are discussed below. In most cases, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques such as the use of extra probes or nucleic acid binding proteins may also be used.

A probe nucleic acid (also referred to herein as a primer nucleic acid) is then contacted to the target sequence to form a hybridization complex. By "primer nucleic acid" herein is meant a probe nucleic acid that will hybridize to some portion, i.e. a domain, of the target sequence. Probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Thus, the assays are generally run under stringency conditions which allows formation of the hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The size of the primer nucleic acid may vary, as will be appreciated by those in the art, in general varying from 5 to 500 nucleotides in length, with primers of between 10 and 100 being preferred, between 15 and 50 being particularly preferred, and from 10 to 35 being especially preferred, depending on the use and amplification technique.

In addition, the different amplification techniques may have further requirements of the primers, as is more fully described below.

Once the hybridization complex between the primer and the target sequence has been formed, an enzyme, sometimes termed an "amplification enzyme", is used to modify the primer. As for all the methods outlined herein, the enzymes may be added at any point during the assay, either prior to, during, or after the addition of the primers. The identification of the enzyme will depend on the amplification technique used, as is more fully outlined below. Similarly, the modification will depend on the amplification technique, as outlined below, although generally the first step of all the reactions herein is an extension of the primer, that is, nucleotides are added to the primer to extend its length.

Once the enzyme has modified the primer to form a modified primer, the hybridization complex is disassociated. Generally, the amplification steps are repeated for a period of time to allow a number of cycles, depending on the number of copies of the original target sequence and the sensitivity of detection, with cycles ranging from 1 to thousands, with from 10 to 100 cycles being preferred and from 20 to 50 cycles being especially preferred.

After a suitable time or amplification, the modified primer is moved to a detection module and incorporated into an assay complex, as is more fully outlined below. The assay complex is attached to a microsphere on an array substrate and then detected, as is described below.

In a preferred embodiment, the amplification is target amplification. Target amplification involves the amplification (replication) of the target sequence to be detected, such that the number of copies of the target sequence is increased. Suitable target amplification techniques include, but are not limited to, the polymerase chain reaction (PCR), strand displacement amplification (SDA), and nucleic acid sequence based amplification (NASBA).

In a preferred embodiment, the target amplification technique is PCR. The polymerase chain reaction (PCR) is widely used and described, and involve the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtration", among others.

In general, PCR may be briefly described as follows. A double stranded target nucleic acid is denatured, generally by raising the temperature, and then cooled in the presence of an excess of a PCR primer, which then hybridizes to the first target strand. A DNA polymerase then acts to extend the primer, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus PCR steps are denaturation, annealing and extension. The particulars of PCR are well known, and include the use of a thermostabile polymerase such as Taq I polymerase and thermal cycling.

Accordingly, the PCR reaction requires at least one PCR primer and a polymerase. Mesoscale PCR devices are described in U.S. Pat. Nos. 5,498,392 and 5,587,128, and WO 97/16561, incorporated by reference.

In a preferred embodiment, the target amplification technique is SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety.

In general, SDA may be described as follows. A single stranded target nucleic acid, usually a DNA target sequence, is contacted with an SDA primer. An "SDA primer" generally has a length of 25-100 nucleotides, with SDA primers of approximately 35 nucleotides being preferred. An SDA primer is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease", as outlined below. The SDA primer then hybridizes to the target sequence. The SDA reaction mixture also contains a polymerase (an "SDA polymerase", as outlined below) and a mixture of all four deoxynucleoside-triphosphates (also called deoxynucleotides or dNTPs, i.e. dATP, dTTP, dCTP and dGTP), at least one species of which is a substituted or modified dNTP; thus, the SDA primer is modified, i.e. extended, to form a modified primer, sometimes referred to herein as a "newly synthesized strand". The substituted dNTP is modified such that it will inhibit cleavage in the strand containing the substituted dNTP but will not inhibit cleavage on the other strand. Examples of suitable substituted dNTPs include, but are not limited, 2' deoxyadenosine 5'-O-(1-thiotriphosphate), 5-methyldeoxycytidine 5'-triphosphate, 2'-deoxyuridine 5'-triphosphate, adn 7-deaza-2'-deoxyguanosine 5'-triphosphate. In addition, the substitution of the dNTP may occur after incorporation into a newly synthesized strand; for example, a methylase may be used to add methyl groups to the synthesized strand. In addition, if all the nucleotides are substituted, the polymerase may have 5'→3' exonuclease activity. However, if less than all the nucleotides are substituted, the polymerase preferably lacks 5'→3' exonuclease activity.

As will be appreciated by those in the art, the recognition site/endonuclease pair can be any of a wide variety of known combinations. The endonuclease is chosen to cleave a strand either at the recognition site, or either 3' or 5' to it, without cleaving the complementary sequence, either because the enzyme only cleaves one strand or because of the incorporation of the substituted nucleotides. Suitable recognition site/endonuclease pairs are well known in the art; suitable endonucleases include, but are not limited to, HincII, HindIII, AvaI, Fnu4HI, TthIIII, NcII, BstXI, BamI, etc. A chart depicting suitable enzymes, and their corresponding recognition sites and the modified dNTP to use is found in U.S. Pat. No. 5,455,166, hereby expressly incorporated by reference.

Once nicked, a polymerase (an "SDA polymerase") is used to extend the newly nicked strand, 5'→3', thereby creating another newly synthesized strand. The polymerase chosen should be able to intiate 5'→3' polymerization at a nick site, should also displace the polymerized strand downstream from the nick, and should lack 5'→3' exonuclease activity (this may be additionally accomplished by the addition of a blocking agent). Thus, suitable polymerases in SDA include, but are not limited to, the Klenow fragment of DNA polymerase I, SEQUENASE 1.0 and SEQUENASE 2.0 (U.S. Biochemical), T5 DNA polymerase and Phi29 DNA polymerase.

Accordingly, the SDA reaction requires, in no particular order, an SDA primer, an SDA polymerase, a nicking endonuclease, and dNTPs, at least one species of which is modified.

In general, SDA does not require thermocycling. The temperature of the reaction is generally set to be high enough to prevent non-specific hybridization but low enough to allow specific hybridization; this is generally from about 37° C. to about 42° C., depending on the enzymes.

In a preferred embodiment, as for most of the amplification techniques described herein, a second amplification reaction can be done using the complementary target sequence, resulting in a substantial increase in amplification during a set period of time. That is, a second primer nucleic acid is hybridized to a second target sequence, that is substantially complementary to the first target sequence, to form a second hybridization complex. The addition of the enzyme, followed by disassociation of the second hybridization complex, results in the generation of a number of newly synthesized second strands.

In this way, a number of target molecules are made, and transferred to a detection module, described below. As is more fully outlined below, these reactions (that is, the products of these reactions) can be detected in a number of ways. In general, either direct or indirect detection of the target products can be done. "Direct" detection as used in this context, as for the other amplification strategies outlined herein, requires the incorporation of a label, either through the incorporation of the label in the amplification primers or by polymerase incorporation of labeled nucleotides into the growing strand. Alternatively, indirect detection proceeds as a sandwich assay, with the newly synthesized strands containing few or no labels. Detection then proceeds via the use of label probes comprising a fluorescent label; these label probes will hybridize either directly to the newly synthesized strand or to intermediate probes such as amplification probes.

In a preferred embodiment, the target amplification technique is nucleic acid sequence based amplification (NASBA). NASBA is generally described in U.S. Pat. No. 5,409,818 and "Profiting from Gene-based Diagnostics", CTB International Publishing Inc., N.J., 1996, both of which are expressly incorporated by reference in their entirety.

In general, NASBA may be described as follows. A single stranded target nucleic acid, usually an RNA target sequence (sometimes referred to herein as "the first target sequence" or "the first template"), is contacted with a first NASBA primer. A "NASBA primer" generally has a length of 25-100 nucleotides, with NASBA primers of approximately 50-75 nucleotides being preferred. The first NASBA primer is preferably a DNA primer that has at its 3' end a sequence that is substantially complementary to the 3' end of the first template. The first NASBA primer has an RNA polymerase promoter at its 5' end. The first NASBA primer is then hybridized to the first template to form a first hybridization complex. The NASBA reaction mixture also includes a reverse transcriptase enzyme (an "NASBA reverse transcriptase") and a mixture of the four dNTPs, such that the first NASBA primer is modified, i.e. extended, to form a modified first primer, comprising a hybridization complex of RNA (the first template) and DNA (the newly synthesized strand).

By "reverse transcriptase" or "RNA-directed DNA polymerase" herein is meant an enzyme capable of synthesizing DNA from a DNA primer and an RNA template. Suitable RNA-directed DNA polymerases include, but are not limited to, avian myloblastosis virus reverse transcriptase ("AMV RT") and the Moloney murine leukemia virus RT.

In addition to the components listed above, the NASBA reaction also includes an RNA degrading enzyme, also sometimes referred to herein as a ribonuclease, that will hydrolyze RNA of an RNA:DNA hybrid without hydrolyzing single- or double-stranded RNA or DNA. Suitable ribonucleases include, but are not limited to, RNase H from *E. coli* and calf thymus.

The ribonuclease degrades the first RNA template in the hybridization complex, resulting in a disassociation of the hybridization complex leaving a first single stranded newly synthesized DNA strand, sometimes referred to herein as "the second template".

In addition, the NASBA reaction also includes a second NASBA primer, generally comprising DNA (although as for all the probes herein, including primers, nucleic acid analogs may also be used). This second NASBA primer has a sequence at its 3' end that is substantially complementary to the 3' end of the second template, and also contains an antisense sequence for a functional promoter and the antisense sequence of a transcription initiation site. Thus, this primer sequence, when used as a template for synthesis of the third DNA template, contains sufficient information to allow specific and efficient binding of an RNA polymerase and initiation of transcription at the desired site. Preferred embodiments utilizes the antisense promoter and transcription initiation site are that of the T7 RNA polymerase, although other RNA polymerase promoters and initiation sites can be used as well, as outlined below.

The second primer hybridizes to the second template, and a DNA polymerase, also termed a "DNA-directed DNA polymerase", also present in the reaction, synthesizes a third template (a second newly synthesized DNA strand), resulting in second hybridization complex comprising two newly synthesized DNA strands.

Finally, the inclusion of an RNA polymerase and the required four ribonucleoside triphosphates (ribonucleotides or NTPs) results in the synthesis of an RNA strand (a third newly synthesized strand that is essentially the same as the first template). The RNA polymerase, sometimes referred to herein as a "DNA-directed RNA polymerase", recognizes the promoter and specifically initiates RNA synthesis at the initiation site. In addition, the RNA polymerase preferably synthesizes several copies of RNA per DNA duplex. Preferred RNA polymerases include, but are not limited to, T7 RNA polymerase, and other bacteriophage RNA polymerases including those of phage T3, phage φ1, *Salmonella* phage sp6, or Pseudomonase phage gh-1.

Accordingly, the NASBA reaction requires, in no particular order, a first NASBA primer, a second NASBA primer comprising an antisense sequence of an RNA polymerase promoter, an RNA polymerase that recognizes the promoter, a reverse transcriptase, a DNA polymerase, an RNA degrading enzyme, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

As outlined herein, the detection of the newly synthesized strands can proceed in several ways. Direct detection can be done in the detection module when the newly synthesized strands comprise ETM labels, either by incorporation into the primers or by incorporation of modified labelled nucleotides into the growing strand. Alternatively, as is more fully outlined below, indirect detection of unlabelled strands (which now serve as "targets" in the detection mode) can occur using a variety of sandwich assay configurations. As will be appreciated by those in the art, it is preferable to detect DNA strands during NASBA since the presence of the ribonuclease makes the RNA strands potentially labile.

In a preferred embodiment, the amplification technique is signal amplification. Signal amplification involves the use of limited number of target molecules as templates to either generate multiple signalling probes or allow the use of multiple signalling probes. Signal amplification strategies include LCR, CPT, Invader™ technology and the use of amplification probes in sandwich assays.

In a preferred embodiment, the signal amplification technique is LCR. The method can be run in two different ways; in a first embodiment, only one strand of a target sequence is used as a template for ligation; alternatively, both strands may be used. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835, and U.S. Ser. Nos. 60/078,102 and 60/073,011, all of which are incorporated by reference.

In a preferred embodiment, the single-stranded target sequence comprises a first target domain and a second target domain, and a first LCR primer and a second LCR primer nucleic acids are added, that are substantially complementary to its respective target domain and thus will hybridize to the target domains. These target domains may be directly adjacent, i.e. contiguous, or separated by a number of nucleotides. If they are non-contiguous, nucleotides are added along with means to join nucleotides, such as a polymerase, that will add the nucleotides to one of the primers. The two LCR primers are then covalently attached, for example using a ligase enzyme such as is known in the art. This forms a first hybridization complex comprising the ligated probe and the target sequence. This hybridization complex is then denatured (disassociated), and the process is repeated to generate a pool of ligated probes. In addition, it may be desirable to have the detection probes, described below, comprise a mismatch at the probe junction site, such that the detection probe cannot be used as a template for ligation.

In a preferred embodiment, LCR is done for two strands of a double-stranded target sequence. The target sequence is denatured, and two sets of probes are added: one set as outlined above for one strand of the target, and a separate set (i.e. third and fourth primer robe nucleic acids) for the other strand of the target. In a preferred embodiment, the first and third probes will hybridize, and the second and fourth probes will hybridize, such that amplification can occur. That is, when the first and second probes have been attached, the ligated probe can now be used as a template, in addition to the second target sequence, for the attachment of the third and fourth probes. Similarly, the ligated third and fourth probes will serve as a template for the attachment of the first and second probes, in addition to the first target strand. In this way, an exponential, rather than just a linear, amplification can occur.

Again, as outlined above, the detection of the LCR reaction can occur directly, in the case where one or both of the primers comprises at least one label, or indirectly, using sandwich assays, through the use of additional probes; that is, the ligated probes can serve as target sequences, and detection may utilize amplification probes, capture probes, capture extender probes, label probes, and label extender probes, etc.

Invader™ technology is based on structure-specific polymerases that cleave nucleic acids in a site-specific manner. Two probes are used: an "invader" probe and a "signalling" probe, that adjacently hybridize to a target sequence with a non-complementary overlap. The enzyme cleaves at the overlap due to its recognition of the "tail", and releases the "tail" with a label. This can then be detected. The Invader™ technology is described in U.S. Pat. Nos. 5,846,717; 5,614,402; 5,719,028; 5,541,311; and 5,843,669, all of which are hereby incorporated by reference.

In a preferred embodiment, the signal amplification technique is CPT. CPT technology is described in a number of patents and patent applications, including U.S. Pat. Nos. 5,011,769, 5,403,711, 5,660,988, and 4,876,187, and PCT published applications WO 95/05480, WO 95/1416, and WO 95/00667, and U.S. Ser. No. 09/014,304, all of which are expressly incorporated by reference in their entirety.

Generally, CPT may be described as follows. A CPT primer (also sometimes referred to herein as a "scissile primer"), comprises two probe sequences separated by a scissile linkage. The CPT primer is substantially complementary to the target sequence and thus will hybridize to it to form a hybridization complex. The scissile linkage is cleaved, without cleaving the target sequence, resulting in the two probe sequences being separated. The two probe sequences can thus be more easily disassociated from the target, and the reaction can be repeated any number of times. The cleaved primer is then detected as outlined herein.

By "scissile linkage" herein is meant a linkage within the scissile probe that can be cleaved when the probe is part of a hybridization complex, that is, when a double-stranded complex is formed. It is important that the scissile linkage cleave only the scissile probe and not the sequence to which it is hybridized (i.e. either the target sequence or a probe sequence), such that the target sequence may be reused in the reaction for amplification of the signal. As used herein, the scissile linkage, is any connecting chemical structure which joins two probe sequences and which is capable of being selectively cleaved without cleavage of either the probe sequences or the sequence to which the scissile probe is hybridized. The scissile linkage may be a single bond, or a multiple unit sequence. As will be appreciated by those in the art, a number of possible scissile linkages may be used.

In a preferred embodiment, the scissile linkage comprises RNA. This system, previously described in as outlined above, is based on the fact that certain double-stranded nucleases, particularly ribonucleases, will nick or excise RNA nucleosides from a RNA:DNA hybridization complex. Of particular use in this embodiment is RNAseH, Exo III, and reverse transcriptase.

In one embodiment, the entire scissile probe is made of RNA, the nicking is facilitated especially when carried out with a double-stranded ribonuclease, such as RNAseH or Exo III. RNA probes made entirely of RNA sequences are particularly useful because first, they can be more easily produced enzymatically, and second, they have more cleavage sites which are accessible to nicking or cleaving by a nicking agent, such as the ribonucleases. Thus, scissile probes made entirely of RNA do not rely on a scissile linkage since the scissile linkage is inherent in the probe.

In a preferred embodiment, when the scissile linkage is a nucleic acid such as RNA, the methods of the invention may be used to detect mismatches, as is generally described in U.S. Pat. Nos. 5,660,988, and WO 95/14106, hereby expressly incorporated by reference. These mismatch detection methods are based on the fact that RNAseH may not bind to and/or cleave an RNA:DNA duplex if there are mismatches present in the sequence. Thus, in the NA$_1$-R-NA$_2$ embodiments, NA$_1$ and NA$_2$ are non-RNA nucleic acids, preferably DNA. Preferably, the mismatch is within the RNA:DNA duplex, but in some embodiments the mismatch is present in an adjacent sequence very close to the desired sequence, close enough to affect the RNAseH (generally within one or two bases). Thus, in this embodiment, the nucleic acid scissile linkage is designed such that the sequence of the scissile linkage reflects the particular sequence to be detected, i.e. the area of the putative mismatch.

In some embodiments of mismatch detection, the rate of generation of the released fragments is such that the methods provide, essentially, a yes/no result, whereby the detection of the virtually any released fragment indicates the presence of the desired target sequence. Typically, however, when there is only a minimal mismatch (for example, a 1-, 2- or 3-base mismatch, or a 3-base deletion), there is some generation of cleaved sequences even though the target sequence is not present. Thus, the rate of generation of cleaved fragments, and/or the final amount of cleaved fragments, is quantified to indicate the presence or absence of the target. In addition, the use of secondary and tertiary scissile probes may be particularly useful in this embodiment, as this can amplify the differences between a perfect match and a mismatch. These methods may be particularly useful in the determination of homozygotic or heterozygotic states of a patient.

In this embodiment, it is an important feature of the scissile linkage that its length is determined by the suspected difference between the target and the probe. In particular, this means that the scissile linkage must be of sufficient length to encompass the suspected difference, yet short enough the scissile linkage cannot inappropriately "specifically hybridize" to the selected nucleic acid molecule when the suspected difference is present; such inappropriate hybridization would permit excision and thus cleavage of scissile linkages even though the selected nucleic acid molecule was not fully complementary to the nucleic acid probe. Thus in a preferred embodiment, the scissile linkage is between 3 to 5 nucleotides in length, such that a suspected nucleotide difference from 1 nucleotide to 3 nucleotides is encompassed by the scissile linkage, and 0, 1 or 2 nucleotides are on either side of the difference.

Thus, when the scissile linkage is nucleic acid, preferred embodiments utilize from 1 to about 100 nucleotides, with from about 2 to about 20 being preferred and from about 5 to about 10 being particularly preferred.

CPT may be done enzymatically or chemically. That is, in addition to RNAseH, there are several other cleaving agents which may be useful in cleaving RNA (or other nucleic acid) scissile bonds. For example, several chemical nucleases have been reported; see for example Sigman et al., Annu. Rev. Biochem. 1990, 59, 207-236; Sigman et al., Chem. Rev. 1993, 93, 2295-2316; Bashkin et al., J. Org. Chem. 1990, 55, 5125-5132; and Sigman et al., Nucleic Acids and Molecular Biology, vol. 3, F. Eckstein and D. M. J. Lilley (Eds), Springer-Verlag, Heidelberg 1989, pp. 13-27; all of which are hereby expressly incorporated by reference.

Specific RNA hydrolysis is also an active area; see for example Chin, Acc. Chem. Res. 1991, 24, 145-152; Breslow et al., Tetrahedron, 1991, 47, 2365-2376; Anslyn et al., Angew. Chem. Int. Ed. Engl., 1997, 36, 432-450; and references therein, all of which are expressly incorporated by reference. Reactive phosphate centers are also of interest in developing scissile linkages, see Hendry et al., Prog. Inorg. Chem.: Bioinorganic Chem. 1990, 31, 201-258 also expressly incorporated by reference.

Current approaches to site-directed RNA hydrolysis include the conjugation of a reactive moiety capable of cleaving phosphodiester bonds to a recognition element capable of sequence-specifically hybridizing to RNA. In most cases, a metal complex is covalently attached to a DNA strand which forms a stable heteroduplex. Upon hybridization, a Lewis acid is placed in close proximity to the RNA backbone to effect hydrolysis; see Magda et al., J. Am. Chem. Soc. 1994, 116, 7439; Hall et al., Chem. Biology 1994, 1, 185-190; Bashkin et al., J. Am. Chem. Soc. 1994, 116, 5981-5982; Hall et al., Nucleic Acids Res. 1996, 24, 3522; Magda et al., J. Am. Chem. Soc. 1997, 119, 2293; and Magda et al., J. Am. Chem. Soc. 1997, 119, 6947, all of which are expressly incorporated by reference.

In a similar fashion, DNA-polyamine conjugates have been demonstrated to induce site-directed RNA strand scission; see for example, Yoshinari et al., J. Am. Chem. Soc. 1991, 113, 5899-5901; Endo et al., J. Org. Chem. 1997, 62, 846; and Barbier et al., J. Am. Chem. Soc. 1992, 114, 3511-3515, all of which are expressly incorporated by reference.

In a preferred embodiment, the scissile linkage is not necessarily RNA. For example, chemical cleavage moieties may be used to cleave basic sites in nucleic acids; see Belmont, et al., New J. Chem. 1997, 21, 47-54; and references therein, all of which are expressly incorporated herein by reference. Similarly, photocleavable moieties, for example, using transition metals, may be used; see Moucheron, et al., Inorg. Chem. 1997, 36, 584-592, hereby expressly by reference.

Other approaches rely on chemical moieties or enzymes; see for example Keck et al., Biochemistry 1995, 34, 12029-12037; Kirk et al., Chem. Commun. 1998, in press; cleavage of G-U basepairs by metal complexes; see Biochemistry, 1992, 31, 5423-5429; diamine complexes for cleavage of RNA; Komiyama, et al., J. Org. Chem. 1997, 62, 2155-2160; and Chow et al., Chem. Rev. 1997, 97, 1489-1513, and references therein, all of which are expressly incorporated herein by reference.

The first step of the CPT method requires hybridizing a primary scissile primer (also called a primary scissile probe) the target. This is preferably done at a temperature that allows both the binding of the longer primary probe and disassociation of the shorter cleaved portions of the primary probe, as will be appreciated by those in the art. As outlined herein, this may be done in solution, or either the target or one or more of the scissile probes may be attached to a solid support. For example, it is possible to utilize "anchor probes" on a solid support on the array substrate that are substantially complementary to a portion of the target sequence, preferably a sequence that is not the same sequence to which a scissile probe will bind.

Similarly, as outlined herein, a preferred embodiment has one or more of the scissile probes attached to a solid support such as a bead (these amplification beads are to be distinguished from the detection array beads outlined below). In this embodiment, the soluble target diffuses to allow the formation of the hybridization complex between the soluble target sequence and the support-bound scissile probe. In this embodiment, it may be desirable to include additional scissile linkages in the scissile probes to allow the release of two or more probe sequences, such that more than one probe sequence per scissile probe may be detected, as is outlined below, in the interests of maximizing the signal.

In this embodiment (and in other techniques herein), preferred methods utilize cutting or shearing techniques to cut the nucleic acid sample containing the target sequence into a size that will allow sufficient diffusion of the target sequence to the surface of a bead. This may be accomplished by shearing the nucleic acid through mechanical forces or by cleaving the nucleic acid using restriction endonucleases. Alternatively, a fragment containing the target may be generated using polymerase, primers and the sample as a template, as in polymerase chain reaction (PCR). In addition, amplification of the target using PCR or LCR or related methods may also be done; this may be particularly useful when the target sequence is present in the sample at extremely low copy numbers. Similarly, numerous techniques are known in the art to increase the rate of mixing and hybridization including agitation, heating, techniques that increase the overall concentration such as precipitation, drying, dialysis, centrifugation, electrophoresis, magnetic bead concentration, etc.

In general, the scissile probes are introduced in a molar excess to their targets (including both the target sequence or other scissile probes, for example when secondary or tertiary scissile probes are used), with ratios of scissile probe:target of at least about 100:1 being preferred, at least about 1000:1 being particularly preferred, and at least about 10,000:1 being especially preferred. In some embodiments the excess of probe:target will be much greater. In addition, ratios such as these may be used for all the amplification techniques outlined herein.

Once the hybridization complex between the primary scissile probe and the target has been formed, the complex is subjected to cleavage conditions. As will be appreciated, this depends on the composition of the scissile probe; if it is RNA, RNAseH is introduced. It should be noted that under certain circumstances, such as is generally outlined in WO 95/00666 and WO 95/00667, hereby incorporated by reference, the use of a double-stranded binding agent such as RNAseH may allow the reaction to proceed even at temperatures above the Tm of the primary probe:target hybridization complex. Accordingly, the addition of scissile probe to the target can be done either first, and then the cleavage agent or cleavage conditions introduced, or the probes may be added in the presence of the cleavage agent or conditions.

The cleavage conditions result in the separation of the two (or more) probe sequences of the primary scissile probe. As a result, the shorter probe sequences will no longer remain hybridized to the target sequence, and thus the hybridization complex will disassociate, leaving the target sequence intact.

The optimal temperature for carrying out the CPT reactions is generally from about 5° C. to about 25° C. below the melting temperatures of the probe:target hybridization complex. This provides for a rapid rate of hybridization and high degree of specificity for the target sequence. The Tm of any particular hybridization complex depends on salt concentration, G-C content, and length of the complex, as is known in the art and outlined herein.

During the reaction, as for the other amplification techniques herein, it may be necessary to suppress cleavage of the probe, as well as the target sequence, by nonspecific nucleases. Such nucleases are generally removed from the sample during the isolation of the DNA by heating or extraction procedures. A number of inhibitors of single-stranded nucleases such as vanadate, inhibitors it-ACE and RNAsin, a placental protein, do not affect the activity of RNAseH. This may not be necessary depending on the purity of the RNAseH and/or the target sample.

These steps are repeated by allowing the reaction to proceed for a period of time. The reaction is usually carried out for about 15 minutes to about 1 hour. Generally, each molecule of the target sequence will turnover between 100 and 1000 times in this period, depending on the length and sequence of the probe, the specific reaction conditions, and the cleavage method. For example, for each copy of the target sequence present in the test sample 100 to 1000 molecules will be cleaved by RNAseH. Higher levels of amplification can be obtained by allowing the reaction to proceed longer, or using secondary, tertiary, or quaternary probes, as is outlined herein.

Upon completion of the reaction, generally determined by time or amount of cleavage, the uncleaved scissile probes must be removed or neutralized prior to detection, such that the uncleaved probe does not bind to a detection probe, causing false positive signals. This may be done in a variety of ways, as is generally described below.

In a preferred embodiment, the separation is facilitated by the use of a solid support (either an internal surface of the device or beads trapped in the device) containing the primary probe. Thus, when the scissile probes are attached to the solid support, the flow of the sample past this solid support can result in the removal of the uncleaved probes.

In a preferred embodiment, the separation is based on gel electrophoresis of the reaction products to separate the longer uncleaved probe from the shorter cleaved probe sequences as is known in the art and described herein.

In a preferred embodiment, the separation is based on strong acid precipitation. This is useful to separate long (generally greater than 50 nucleotides) from smaller fragments (generally about 10 nucleotides). The introduction of a strong acid such as trichloroacetic acid into the solution (generally from a storage module) causes the longer probe to precipitate, while the smaller cleaved fragments remain in solution. The use of flits or filters can to remove the precipitate, and the cleaved probe sequences can be quantitated.

In a preferred embodiment, the scissile probe contains both a detectable label and an affinity binding ligand or moiety, such that an affinity support is used to carry out the separation. In this embodiment, it is important that the detectable label used for detection is not on the same probe sequence that contains the affinity moiety, such that removal of the uncleaved probe, and the cleaved probe containing the affinity moiety, does not remove all the detectable labels. Suitable affinity moieties include, but are not limited to, biotin, avidin, streptavidin, lectins, haptens, antibodies, etc. The binding partner of the affinity moiety is attached to a solid support (again, either an internal surface of the device or to beads trapped within the device) and the flow of the sample past this support is used to pull out the uncleaved probes, as is known in the art. The cleaved probe sequences, which do not contain the affinity moiety, remain in solution and then can be detected as outlined below.

In a preferred embodiment, similar to the above embodiment, a separation sequence of nucleic acid is included in the scissile probe, which is not cleaved during the reaction. A nucleic acid complementary to the separation sequence is attached to a solid support and serves as a catcher sequence. Preferably, the separation sequence is added to the scissile probes, and is not recognized by the target sequence, such that a generalized catcher sequence may be utilized in a variety of assays.

In a preferred embodiment, the uncleaved probe is neutralized by the addition of a substantially complementary neutralization nucleic acid, generally from a storage module. This is particularly useful in embodiments utilizing capture sequences, separation sequences, and one-step systems, as the complement to a probe containing capture sequences forms hybridization complexes that are more stable due to its length than the cleaved probe sequence:detection probe complex. What is important is that the uncleaved probe is not available for binding to a detection probe specific for cleaved sequences. Thus, in one embodiment, this step occurs in the detection module and the neutralization nucleic acid is a detection probe on the surface of the array substrate, at a separate "address", such that the signal from the neutralization hybridization complex does not contribute to the signal of the cleaved fragments. Alternatively, the neutralization nucleic acid may be attached to a solid support; the sample flowed past the neutralization surface to quench the reaction, and thus do not enter the detection module.

After removal or neutralization of the uncleaved probe, detection proceeds via the addition of the cleaved probe sequences to the detection module, as outlined below.

In a preferred embodiment, no higher order probes are used, and detection is based on the probe sequence(s) of the primary primer. In a preferred embodiment, at least one, and preferably more, secondary probes (also referred to herein as secondary primers) are used. The secondary scissile probes may be added to the reaction in several ways. It is important that the secondary scissile probes be prevented from hybridizing to the uncleaved primary probes, as this results in the generation of false positive signal. In a preferred embodiment, the primary and secondary probes are bound to solid supports. It is only upon hybridization of the primary probes with the target, resulting in cleavage and release of primary probe sequences from the bead, that the now diffusible primary probe sequences may bind to the secondary probes. In turn, the primary probe sequences serve as targets for the secondary scissile probes, resulting in cleavage and release of secondary probe sequences. In an alternate embodiment, the complete reaction is done in solution. In this embodiment, the primary probes are added, the reaction is allowed to proceed for some period of time, and the uncleaved primary scissile probes are removed, as outlined above. The secondary probes are then added, and the reaction proceeds. The secondary uncleaved probes are then removed, and the cleaved sequences are detected as is generally outlined herein. In a preferred embodiment, at least one, and preferably more, tertiary probes are used. The tertiary scissile probes may be added to the reaction in several ways. It is important that the tertiary scissile probes be prevented from hybridizing to the uncleaved secondary probes, as this results in the generation of false positive signal. These methods are generally done as outlined above. Similarly, quaternary probes can be used as above.

Thus, CPT requires, again in no particular order, a first CPT primer comprising a first probe sequence, a scissile linkage and a second probe sequence; and a cleavage agent.

In this manner, CPT results in the generation of a large amount of cleaved primers, which then can be detected as outlined below.

In a preferred embodiment, the signal amplification technique is a "sandwich" assay, as is generally described in U.S. Ser. No. 60/073,011 and in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. Although sandwich assays do not result in the alteration of primers, sandwich assays can be considered signal amplification techniques since multiple signals (i.e. label probes) are bound to a single target, resulting in the amplification of the signal. Sandwich assays are used when the target sequence comprises little or no detectable labels; that is, when a secondary probe, comprising the labels, is used to generate the signal.

As discussed herein, it should be noted that the sandwich assays can be used for the detection of primary target sequences (e.g. from a patient sample), or as a method to detect the product of an amplification reaction as outlined above; thus for example, any of the newly synthesized strands outlined above, for example using PCR, LCR, NASBA, SDA, etc., may be used as the "target sequence" in a sandwich assay.

Generally, sandwich signal amplification techniques may be described as follows. The reactions described below can occur either in the reaction module, with subsequent transfer to the detection module for detection, or in the detection module with the addition of the required components; for clarity, these are discussed together.

As a preliminary matter, as is more fully described below, capture extender probes may be added to the target sequence for attachment to the beads in the detection module.

The methods include the addition of an amplifier probe, which is hybridized to the target sequence, either directly, or through the use of one or more label extender probes, which serves to allow "generic" amplifier probes to be made. Preferably, the amplifier probe contains a multiplicity of amplification sequences, although in some embodiments, as described below, the amplifier probe may contain only a single amplification sequence, or at least two amplification sequences. The amplifier probe may take on a number of different forms; either a branched conformation, a dendrimer conformation, or a linear "string" of amplification sequences. Label probes comprising detectable labels then hybridize to the amplification sequences (or in some cases the label probes hybridize directly to the target sequence), and the labels are detected as is more fully outlined below.

As will be appreciated by those in the art, the systems of the invention may take on a large number of different configurations. In general, there are three types of systems that can be used: (1) "non-sandwich" systems (also referred to herein as "direct" detection) in which the target sequence itself is labeled (again, either because the primers comprise labels or due to the incorporation of labeled nucleotides into the newly synthesized strand); (2) systems in which label probes directly bind to the target analytes; and (3) systems in which label probes are indirectly bound to the target sequences, for example through the use of amplifier probes.

Accordingly, the present invention provides compositions comprising an amplifier probe. By "amplifier probe" or "nucleic acid multimer" or "amplification multimer" or grammatical equivalents herein is meant a nucleic acid probe that is used to facilitate signal amplification. Amplifier probes comprise at least a first single-stranded nucleic acid probe sequence, as defined below, and at least one single-stranded nucleic acid amplification sequence, with a multiplicity of amplification sequences being preferred.

Amplifier probes comprise a first probe sequence that is used, either directly or indirectly, to hybridize to the target sequence. That is, the amplifier probe itself may have a first probe sequence that is substantially complementary to the target sequence, or it has a first probe sequence that is substantially complementary to a portion of an additional probe, in this case called a label extender probe, that has a first portion that is substantially complementary to the target sequence. In a preferred embodiment, the first probe sequence of the amplifier probe is substantially complementary to the target sequence.

In general, as for all the probes herein, the first probe sequence is of a length sufficient to give specificity and stability. Thus generally, the probe sequences of the invention that are designed to hybridize to another nucleic acid (i.e. probe sequences, amplification sequences, portions or domains of larger probes) are at least about 5 nucleosides long, with at least about 10 being preferred and at least about 15 being especially preferred.

In a preferred embodiment, several different amplifier probes are used, each with first probe sequences that will hybridize to a different portion of the target sequence. That is, there is more than one level of amplification; the amplifier probe provides an amplification of signal due to a multiplicity of labelling events, and several different amplifier probes, each with this multiplicity of labels, for each target sequence is used. Thus, preferred embodiments utilize at least two different pools of amplifier probes, each pool having a different probe sequence for hybridization to different portions of the target sequence; the only real limitation on the number of different amplifier probes will be the length of the original target sequence. In addition, it is also possible that the different amplifier probes contain different amplification sequences, although this is generally not preferred.

In a preferred embodiment, the amplifier probe does not hybridize to the sample target sequence directly, but instead hybridizes to a first portion of a label extender probe. This is particularly useful to allow the use of "generic" amplifier probes, that is, amplifier probes that can be used with a variety of different targets. This may be desirable since several of the amplifier probes require special synthesis techniques, for example when branched structures are used. Thus, the addition of a relatively short probe as a label extender probe is preferred. Thus, the first probe sequence of the amplifier probe is substantially complementary to a first portion or domain of a first label extender single-stranded nucleic acid probe. The label extender probe also contains a second portion or domain that is substantially complementary to a portion of the target sequence. Both of these portions are preferably at least about 10 to about 50 nucleotides in length, with a range of about 15 to about 30 being preferred. The terms "first" and "second" are not meant to confer an orientation of the sequences with respect to the 5'-3' orientation of the target or probe sequences. For example, assuming a 5'-3' orientation of the complementary target sequence, the first portion may be located either 5' to the second portion, or 3' to the second portion. For convenience herein, the order of probe sequences are generally described from left to right.

In a preferred embodiment, more than one label extender probe-amplifier probe pair may be used. That is, a plurality of label extender probes may be used, each with a portion that is substantially complementary to a different portion of the target sequence; this can serve as another level of amplification. Thus, a preferred embodiment utilizes pools of at least two label extender probes, with the upper limit being set by the length of the target sequence.

In a preferred embodiment, more than one label extender probe is used with a single amplifier probe to reduce nonspecific binding, as is generally outlined in U.S. Pat. No. 5,681,697, incorporated by reference herein. In this embodiment, a first portion of the first label extender probe hybridizes to a first portion of the target sequence, and the second portion of the first label extender probe hybridizes to a first probe sequence of the amplifier probe. A first portion of the second label extender probe hybridizes to a second portion of the target sequence, and the second portion of the second label extender probe hybridizes to a second probe sequence of the amplifier probe. These form structures sometimes referred to as "cruciform" structures or configurations, and are generally done to confer stability when large branched or dendrimeric amplifier probes are used.

In addition, as will be appreciated by those in the art, the label extender probes may interact with a preamplifier probe, described below, rather than the amplifier probe directly.

Similarly, as outlined above, a preferred embodiment utilizes several different amplifier probes, each with first probe sequences that will hybridize to a different portion of the label extender probe. In addition, as outlined above, it is also possible that the different amplifier probes contain different amplification sequences, although this is generally not preferred.

In addition to the first probe sequence, the amplifier probe also comprises at least one amplification sequence. An "amplification sequence" or "amplification segment" or grammatical equivalents herein is meant a sequence that is used, either directly or indirectly, to bind to a first portion of a label probe as is more fully described below (although in some cases the amplification sequence may bind to a detection probe). Preferably, the amplifier probe comprises a multiplicity of amplification sequences, with from about 3 to about 1000 being preferred, from about 10 to about 100 being particularly preferred, and about 50 being especially preferred. In some cases, for example when linear amplifier probes are used, from 1 to about 20 is preferred with from about 5 to about 10 being particularly preferred.

The amplification sequences may be linked to each other in a variety of ways, as will be appreciated by those in the art. They may be covalently linked directly to each other, or to intervening sequences or chemical moieties, through nucleic acid linkages such as phosphodiester bonds, PNA bonds, etc., or through interposed linking agents such amino acid, carbohydrate or polyol bridges, or through other cross-linking agents or binding partners. The site(s) of linkage may be at the ends of a segment, and/or at one or more internal nucleotides in the strand. In a preferred embodiment, the amplification sequences are attached via nucleic acid linkages.

In a preferred embodiment, branched amplifier probes are used, as are generally described in U.S. Pat. No. 5,124,246, hereby incorporated by reference. Branched amplifier probes may take on "fork-like" or "comb-like" conformations. "Fork-like" branched amplifier probes generally have three or more oligonucleotide segments emanating from a point of origin to form a branched structure. The point of origin may be another nucleotide segment or a multifunctional molecule to whcih at least three segments can be covalently or tightly bound. "Comb-like" branched amplifier probes have a linear backbone with a multiplicity of sidechain oligonucleotides extending from the backbone. In either conformation, the pendant segments will normally depend from a modified nucleotide or other organic moiety having the appropriate functional groups for attachment of oligonucleotides. Furthermore, in either conformation, a large number of amplification sequences are available for binding, either directly or indirectly, to detection probes. In general, these structures are made as is known in the art, using modified multifunctional nucleotides, as is described in U.S. Pat. Nos. 5,635,352 and 5,124,246, among others.

In a preferred embodiment, dendrimer amplifier probes are used, as are generally described in U.S. Pat. No. 5,175,270, hereby expressly incorporated by reference. Dendrimeric amplifier probes have amplification sequences that are attached via hybridization, and thus have portions of double-stranded nucleic acid as a component of their structure. The outer surface of the dendrimer amplifier probe has a multiplicity of amplification sequences.

In a preferred embodiment, linear amplifier probes are used, that have individual amplification sequences linked end-to-end either directly or with short intervening sequences to form a polymer. As with the other amplifier configurations, there may be additional sequences or moieties between the amplification sequences.

In one embodiment, the linear amplifier probe has a single amplification sequence. However, in a preferred embodiment, linear amplifier probes comprise a multiplicity of amplification sequences.

In addition, the amplifier probe may be totally linear, totally branched, totally dendrimeric, or any combination thereof.

The amplification sequences of the amplifier probe are used, either directly or indirectly, to bind to a label probe to allow detection. In a preferred embodiment, the amplification sequences of the amplifier probe are substantially complementary to a first portion of a label probe. Alternatively, amplifier extender probes are used, that have a first portion that binds to the amplification sequence and a second portion that binds to the first portion of the label probe.

In addition, the compositions of the invention may include "preamplifier" molecules, which serves a bridging moiety between the label extender molecules and the amplifier probes.

Thus, label probes are either substantially complementary to an amplification sequence or to a portion of the target sequence.

Detection of the amplification reactions of the invention, including the direct detection of amplification products and indirect detection utilizing label probes (i.e. sandwich assays), is done by detecting assay complexes comprising labels that are attached to a component of the hybridization complex.

In addition, as described in U.S. Pat. No. 5,587,128, the reaction chamber may comprise a composition, either in solution or adhered to the surface of the reaction chamber, that prevents the inhibition of an amplification reaction by the composition of the well. For example, the wall surfaces may be coated with a silane, for example using a silanization reagent such as dimethylchlorosilane, or coated with a siliconizing reagent such as Aquasil™ or Surfacil™ (Pierce, Rockford, Ill.), which are organosilanes containing a hydrolyzable group. This hydrolyzable group can hydrolyze in solution to form a silanol that can polymerize and form a tightly bonded film over the surface of the chamber. The coating may also include a blocking agent that can react with the film to further reduce inhibition; suitable blocking agents include amino acid polymers and polymers such as polyvinylpyrrolidone, polyadenylic acid and polymaleimide. Alternatively, for silicon substrates, a silicon oxide film may be provided on the walls, or the reaction chamber can be coated with a relatively inert polymer such as a polyvinylchloride. In addition, it may be desirable to add blocking polynucleotides to occupy any binding sites on the surface of the chamber.

In this and other embodiments, at least one heating and/or cooling module may be used, that is either part of the reaction chamber or separate but can be brought into spatial proximity to the reaction module. Suitable heating modules are described in U.S. Pat. Nos. 5,498,392 and 5,587,128, and WO 97/16561, incorporated by reference, and may comprise electrical resistance heaters, pulsed lasers or other sources of electromagnetic energy directed to the reaction chamber. It should also be noted that when heating elements are used, it may be desirable to have the reaction chamber be relatively shallow, to facilitate heat transfer; see U.S. Pat. No. 5,587,128.

In a preferred embodiment, the biological reaction chamber allows enzymatic cleavage or alteration of the target analyte. For example, restriction endonucleases may be used to cleave target nucleic acids comprising target sequences, for example genomic DNA, into smaller fragments to facilitate either amplification or detection. Alternatively, when the target analyte is a protein, it may be cleaved by a protease. Other types of enzymatic hydrolysis may also be done, depending on the composition of the target analyte. In addition, as outlined herein, the target analyte may comprise an enzyme and the reaction chamber comprises a substrate that is then cleaved to form a detectable product.

In addition, in one embodiment the reaction module includes a chamber for the physical alteration of all or part of the sample, for example for shearing genomic or large nucleic acids, UV crosslinking, etc.

In a preferred embodiment, the devices of the invention include at least one fluid pump. Pumps generally fall into two categories: "on chip" and "off chip"; that is, the pumps (generally electrode based pumps) can be contained within the device itself, or they can be contained on an apparatus into which the device fits, such that alignment occurs of the required flow channels to allow pumping of fluids.

In a preferred embodiment, the pumps are contained on the device itself. These pumps are generally electrode based pumps; that is, the application of electric fields can be used to move both charged particles and bulk solvent, depending on the composition of the sample and of the device. Suitable on chip pumps include, but are not limited to, electroosmotic (EO) pumps and electrohydrodynamic (EHD) pumps; these electrode based pumps have sometimes been referred to in the art as "electrokinetic (EK) pumps". All of these pumps rely on configurations of electrodes placed along a flow channel to result in the pumping of the fluids comprising the sample components. As is described in the art, the configurations for each of these electrode based pumps are slightly different; for example, the effectiveness of an EHD pump depends on the spacing between the two electrodes, with the closer together they are, the smaller the voltage required to be applied to effect fluid flow. Alternatively, for EO pumps, the spacing between the electrodes should be larger, with up to one-half the length of the channel in which fluids are being moved, since the electrode are only involved in applying force, and not, as in EHD, in creating charges on which the force will act.

In a preferred embodiment, an electroosmotic pump is used. Electroosmosis (EO) is based on the fact that the surface of many solids, including quartz, glass and others, become variously charged, negatively or positively, in the presence of ionic materials. The charged surfaces will attract oppositely charged counterions in aqueous solutions. Applying a voltage results in a migration of the counterions to the oppositely chaged electrode, and moves the bulk of the fluid as well. The volume flow rate is proportional to the current, and the volume flow generated in the fluid is also proportional to the applied voltage. Electroosmostic flow is useful for liquids having some conductivity is and generally not applicable for non-polar solvents. EO pumps are described in U.S. Pat. Nos. 4,908,112 and 5,632,876, PCT US95/14586 and WO97/43629, incorporated by reference.

In a preferred embodiment, an electrohydrodynamic (EHD) pump is used. In EHD, electrodes in contact with the fluid transfer charge when a voltage is applied. This charge transfer occurs either by transfer or removal of an electron to or from the fluid, such that liquid flow occurs in the direction from the charging electrode to the oppositely charged electrode. EHD pumps can be used to pump resistive fluids such as non-polar solvents. EHD pumps are described in U.S. Pat. No. 5,632,876, hereby incorporated by reference.

The electrodes of the pumps preferably have a diameter from about 25 microns to about 100 microns, more preferably from about 50 microns to about 75 microns. Preferably, the electrodes protrude from the top of a flow channel to a depth of from about 5% to about 95% of the depth of the channel, with from about 25% to about 50% being preferred. In addition, as described in PCT US95/14586, an electrode-based internal pumping system can be be integrated into the liquid distribution system of the devices of the invention with flow-rate control at multiple pump sites and with fewer complex electronics if the pumps are operated by applying pulsed voltages across the electrodes; this gives the additional advantage of ease of integration into high density systems, reductions in the amount of electrolysis that occurs at electrodes, reductions in thermal convenction newar the electrodes, and the ability to use simpler drivers, and the ability to use both simple and complex pulse wave geometries.

The voltages required to be applied to the electrodes cause fluid flow depends on the geometry of the electrodes and the properties of the fluids to be moved. The flow rate of the fluids is a function of the amplitude of the applied voltage between electrode, the electrode geometery and the fluid properties, which can be easily determined for each fluid. Test voltages used may be up to about 1500 volts, but an operating voltage of about 40 to 300 volts is desirable. An analog driver is generally used to vary the voltage applied to the pump from a DC power source. A transfer function for each fluid is determined experimentally as that applied voltage that produces the desired flow or fluid pressue to the fluid being moved in the channel. However, an analog driver is generally required for each pump along the channel and is suitable an operational amplifier.

In a preferred embodiment, a micromechanical pump is used, either on- or off-chip, as is known in the art.

In a preferred embodiment, an "off-chip" pump is used. For example, the devices of the invention may fit into an apparatus or appliance that has a nesting site for holding the device, that can register the ports (i.e. sample inlet ports, fluid inlet ports, and waste outlet ports) and electrode leads. The apparatus can including pumps that can apply the sample to the device; for example, can force cell-containing samples into cell lysis modules containing protrusions, to cause cell lysis upon application of sufficient flow pressure. Such pumps are well known in the art.

In a preferred embodiment, the devices of the invention include at least one fluid valve that can control the flow of fluid into or out of a module of the device. A variety of valves are known in the art. For example, in one embodiment, the valve may comprise a capillary barrier, as generally described in PCT US97/07880, incorporated by reference. In this embodiment, the channel opens into a larger space designed to favor the formation of an energy minimizing liquid surface such as a meniscus at the opening. Preferably, capillary barriers include a dam that raises the vertical height of the channel immediated before the opening into a larger space such a chamber. In addition, as described in U.S. Pat. No. 5,858,195, incorporated herein by reference, a type of "virtual valve" can be used.

In a preferred embodiment, the devices of the invention include sealing ports, to allow the introduction of fluids, including samples, into any of the modules of the invention, with subsequent closure of the port to avoid the loss of the sample.

In a preferred embodiment, the devices of the invention include at least one storage modules for assay reagents. These are connected to other modules of the system using flow channels and may comprise wells or chambers, or extended flow channels. They may contain any number of reagents, buffers, salts, etc.

In a preferred embodiment, the devices of the invention include a mixing module; again, as for storage modules, these may be extended flow channels (particularly useful for timed mixing), wells or chambers. Particularly in the case of extended flow channels, there may be protrusions on the side of the channel to cause mixing.

In a preferred embodiment, the devices of the invention include a detection module. The present invention is directed to methods and compositions useful in the detection of biological target analyte species such as nucleic acids and proteins. In general, the detection module is based on work outlined in U.S. Ser. Nos. 09/151,877; 09/187,289 and 09/189,543; PCT US98/21193; PCT US99/04473 and PCT US98/05025, all of which are hereby incorporated by reference in their entirety.

The detection modules of the present invention comprise an array substrate with a surface comprising discrete sites and a population of array microspheres (sometimes referred to herein as beads) distributed on the array surface. The detection module of the microfluidic devices described herein are based on previous work comprising a bead-based analytic chemistry system in which beads, also termed microspheres, carrying different chemical functionalities are distributed on an array substrate comprising a patterned surface of discrete sites that can bind the individual microspheres. The beads are generally put onto the substrate randomly, and thus several different methodologies can be used to "decode" the arrays. In one embodiment, unique optical signatures are incorporated into the beads, generally fluorescent dyes, that could be used to identify the chemical functionality on any particular bead. This allows the synthesis of the candidate agents (i.e. compounds such as nucleic acids and antibodies) to be divorced from their placement on an array, i.e. the candidate agents may be synthesized on the beads, and then the beads are randomly distributed on a patterned surface. Since the beads are first coded with an optical signature, this means that the array can later be "decoded", i.e. after the array is made, a correlation of the location of an individual site on the array with the bead or candidate agent at that particular site can be made. This means that the beads may be randomly distributed on the array, a fast and inexpensive process as compared to either the in situ synthesis or spotting techniques of the prior art. These methods are generally outlined in PCT US98/05025, PCT/US99/20914, U.S. Pat. No. 6,023,540 and U.S. Ser. Nos. 09/151,877 and 09/450,829, all of which are expressly incorporated herein by reference.

However, the drawback to these methods is that for a very high density array, the system requires a large number of different optical signatures, which may be difficult or time-consuming to utilize. Accordingly, the present invention also provides several improvements over these methods, generally directed to methods of coding and decoding the arrays. That is, as will be appreciated by those in the art, the placement of the bioactive agents is generally random, and thus a coding/decoding system is required to identify the bioactive agent at each location in the array. This may be done in a variety of ways, as is more fully outlined below, and generally includes: a) the use a decoding binding ligand (DBL), generally directly labeled, that binds to either the bioactive agent or to identifier binding ligands (IBLs) attached to the beads; b) positional decoding, for example by either targeting the placement of beads (for example by using photoactivatible or photocleavable moieties to allow the selective addition of beads to particular locations), or by using either sub-bundles or selective loading of the sites, as are more fully outlined below; c) selective decoding, wherein only those beads that bind to a target are decoded; or d) combinations of any of these. In some cases, as is more fully outlined below, this decoding may occur for all the beads, or only for those that bind a particular target analyte. Similarly, this may occur either prior to or after addition of a target analyte.

In the detection module of the present invention, "decoding" can use optical signatures, decoding binding ligands that are added during a decoding step, or a combination of these methods. The decoding binding ligands will bind either to a distinct identifier binding ligand partner that is placed on the beads, or to the bioactive agent itself, for example when the beads comprise single-stranded nucleic acids as the bioactive agents. The decoding binding ligands are either directly or indirectly labeled, and thus decoding occurs by detecting the presence of the label. By using pools of decoding binding ligands in a sequential fashion, it is possible to greatly minimize the number of required decoding steps.

Once the identity (i.e. the actual agent) and location of each microsphere in the array has been fixed, the detection array is exposed to samples containing the target analytes, although as outlined below, this can be done prior to or during the analysis as well. The components of the microfluidic device may be used in the decoding as desired. The target analytes will bind to the bioactive agents as is more fully outlined below, and results in a change in the optical signal of a particular bead, resulting in detection.

Accordingly, the present invention provides detection modules comprising arrays comprising at least a first substrate with a surface comprising a plurality of assay locations. By "array" herein is meant a plurality of candidate agents in an array format; the size of the array will depend on the composition and end use of the array. Arrays containing from about 2 different bioactive agents (i.e. different beads) to many millions can be made, with very large fiber optic arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, (with all numbers being per square centimeter) with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 µm or less (with beads of 200 nm possible) can be used, and very small fibers are known, it is possible to have as many as 250,000 or more (in some instances, 1 million) different fibers and beads in a 1 mm$^2$ fiber optic bundle, with densities of greater than 15,000,000 individual beads and fibers (again, in some instances as many as 25-50 million) per 0.5 cm$^2$ obtainable.

By "array substrate" or "array solid support" or other grammatical equivalents herein is meant any material that can be modified to contain discrete individual sites appropriate for the attachment or association of beads and is amenable to at least one detection method as outlined herein. As will be appreciated by those in the art, the number of possible array substrates is very large. Possible array substrates include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluorescese. The array substrates may be the same as the device substrates, or they may be different. If different, they may be attached to the device in any number of ways, as will be appreciated by those in the art, including, but not limited to, the use of adhesives, fusing the two materials together (for example using heat or organic solvents).

Generally the substrate is flat (planar), although as will be appreciated by those in the art, other configurations of assay substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred assay substrates include optical fiber bundles as discussed below, and flat planar substrates such as glass, polystyrene and other plastics and acrylics.

Accordingly, in a preferred embodiment, the array comprises a fiber optic bundle. That is, the microfluidic chip and a fiber optic bundle as described in WO/98/40726 and WO/00/016101 are combined to form the device of the invention.

In one embodiment, the microfluidic chip and the fiber optic bundle are prepared separately and then combined. To combine the fiber optic bundle with the microfluidic chip, a hole is opened in the chip that intersects with a channel in the chip. In a preferred embodiment, the hole is perpendicular to the channel. In addition, it is preferred that the hole penetrate only through the first wall of the channel. Finally, it is preferred that the diameter of the hole match the diameter of the fiber optic bundle. When the diameter of the hole does not precisely match the size of the fiber optic bundle, adapter fittings may be used to facilitate the connection of the chip with the fiber optic bundle.

Once the opening has been formed in the chip, the fiber optic bundle is inserted into the hole. In a preferred embodiment, the surface fo the bundle matches or is aligned with the first wall of the channel.

The bundle is attached to the chip through any of a number of ways as is known in the art. These include for example, adhesive or press fittings.

In one embodiment, microspheres are distributed on the array or bundle prior to connecting to the microfluidic chip. Alternatively, the beads are distributed following connection of the bundle to the chip as is outlined below.

In another preferred embodiment, the substrate comprising discrete sites is the microfluidic chamber itself. That is, a channel of the microfluidic device is modified so as to contain wells for distribution of the beads. In one embodiment the wells are made by etching or molding the surface of the chamber as described herein. Alternatively, pre-made wells are added, i.e., adfixed, to the floor of the chamber.

The assay substrate comprises an assay surface comprising a plurality of assay locations, i.e. the location where the assay for the detection of a target analyte will occur. The assay locations are generally physically separated from each other, although other configurations (hydrophobicity/hydrophilicity, etc.) can be used to separate the assay locations.

In a preferred embodiment, the assay substrate is a slice or a section an optical fiber bundle or array, as is generally described in U.S. Ser. Nos. 08/944,850, 08/519,062 and 09/287,573, PCT US98/05025, PCT/US98/21193 and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

In a preferred embodiment, the assay surface comprises a plurality of discrete sites. That is, at least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the array substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the array substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, for example when the array substrate is a fiber optic bundle, the surface of the substrate is a terminal end of the fiber bundle, as is generally described in PCT US98/05025, PCT/US99/20914, U.S. Pat. No. 6,023,540 and U.S. Ser. Nos. 09/151,877 and 09/450,829, all of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the array substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In a preferred embodiment, the substrate is configured to allow mixing of the sample, reagents, microspheres, etc. That is, in a variety of embodiments, mixing or sample turbulence is desirable. This can be accomplished in a variety of ways. In a preferred embodiment, the substrate comprises raised microstructures such as vertical "posts" or weirs, or other configurations that create sample turbulence, such as edged depressions. These structures may be configured with respect to the chamber such that the flow of the sample past the array causes mixing or sample turbulence. For example, in one embodiment the detection surface is "sunken" or "recessed" with respect to the chamber, such that the flow of the sample past the electrode causes mixing. In a preferred embodiment, vertical "posts" or "pins" are included, to create sample turbulence.

These microstructures can be included anywhere within the device, including within chambers or channels, and may be formed from any substrate as described herein by known microstructure fabrication techniques. In one embodiment, these microstructures are formed or coated from materials different from the substrate to prevent undesirable interactions with the beads or sample; for example, in a preferred embodiment, the posts are made of metal.

The compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon may all be used. "*Microsphere Detection Guide*" from Bangs Laboratories, Fishers IN is a helpful guide.

The beads need not be spherical; irregular particles may be used. In addition, the beads may be porous, thus increasing the surface area of the bead available for either bioactive agent attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a bioactive agent, although as will be appreciated by those in the art, there may be some microspheres which do not contain a bioactive agent, depending the on the synthetic methods. By "candidate bioactive agent" or "bioactive agent" or "chemical functionality" or "binding ligand" herein is meant as used herein describes any molecule, e.g., protein, oligopeptide, small organic molecule, coordination complex, polysaccharide, polynucleotide, etc. which can be attached to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and proteins.

Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins, as defined above.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents are used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least $10^9$ different bioactive agents are simultaneously analyzed in the subject methods. Preferred methods maximize library size and diversity.

In a preferred embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids as defined above (generally called "probe nucleic acids" or "candidate probes" herein). As described above generally for proteins, nucleic acid bioactive agents may be naturally occurring nucleic acids, random nucleic acids, or "biased" random nucleic acids. For example, digests of procaryotic or eukaryotic genomes may be used as is outlined above for proteins.

When the bioactive agents are nucleic acids, they are designed to be substantially complementary to target sequences. The term 'target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent. The numbers of beads for each subpopulation will vary. Those of skill in the art will appreciate that the random distribution of the beads on the array substrate will generally follow a Poisson distribution, and thus any particular subpopulation will have the same number or a different number of beads on the array substrate. Similarly, the redundancy of the array will vary with the application for which it is used. Preferred embodiments have at least two beads of each subpopulation on the array, with from at least about three to about fifty being preferred, from about five to about twenty being preferred, and from about eight to about ten being particularly preferred.

As will be appreciated by those in the art, the bioactive agents may either be synthesized directly on the beads, or they may be made and then attached after synthesis. In a preferred embodiment, linkers are used to attach the bioactive agents to the beads, to allow both good attachment, sufficient flexibility to allow good interaction with the target molecule, and to avoid undesirable binding reactions.

In a preferred embodiment, the bioactive agents are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the bioactive agents are synthesized first, and then covalently attached to the beads. As will be appreciated by those in the art, this will be done depending on the composition of the bioactive agents and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, ce-haloacetyls, and pyridyl disulfides (see for example the 1994 Pierce Chemical Company catalog, technical section on cross-linkers, pages 155-200, incorporated herein by reference) which can be used to attach cysteine containing proteinaceous agents to the support. Alternatively, an amino group on the candidate agent may be used for attachment to an amino group on the surface. For example, a large number of stable bifunctional groups are well known in the art, including homobifunctional and heterobifunctional linkers (see Pierce Catalog and Handbook, pages 155-200). In an additional embodiment, carboxyl groups (either from the surface or from the candidate agent) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems,* 7(4):275-308 (1991), expressly incorporated herein). Proteinaceous candidate agents may also be attached using other techniques known in the art, for example for the attachment of antibodies to polymers; see Slinkin et al., *Bioconj. Chem.* 2:342-348 (1991); Torchilin et al., supra; Trubetskoy et al., *Bioconj Chem.* 3:323-327 (1992); King et al., *Cancer Res.* 54:6176-6185 (1994); and Wilbur et al., *Bioconjugate Chem.* 5:220-235 (1994), all of which are hereby expressly incorporated by reference). It should be understood that the candidate agents may be attached in a variety of ways, including those listed above. What is important is that manner of attachment does not significantly alter the functionality of the candidate agent; that is, the candidate agent should be attached in such a flexible manner as to allow its interaction with a target.

Specific techniques for immobilizing enzymes on microspheres are known in the prior art. In one case, $NH_2$ surface chemistry microspheres are used. Surface activation is achieved with a 2.5% glutaraldehyde in phosphate buffered saline (10 mM) providing a pH of 6.9. (138 mM NaCl, 2.7 mM, KCl). This is stirred on a stir bed for approximately 2 hours at room temperature. The microspheres are then rinsed with ultrapure water plus 0.01% tween 20 (surfactant)-

0.02%, and rinsed again with a pH 7.7 PBS plus 0.01% tween 20. Finally, the enzyme is added to the solution, preferably after being prefiltered using a 0.45 μm amicon micropure filter.

In some embodiments, the beads may additionally comprise an optical signature, that can be used to identify the bioactive agent; see for example PCT US98/05025, PCT/US99/20914, U.S. Pat. No. 6,023,540 and U.S. Ser. Nos. 09/151,877 and 09/450,829, all of which are expressly incorporated herein by reference.

In some embodiments, the microspheres may additionally comprise identifier binding ligands for use in certain decoding systems. By "identifier binding ligands" or "IBLs" herein is meant a compound that will specifically bind a corresponding decoder binding ligand (DBL) to facilitate the elucidation of the identity of the bioactive agent attached to the bead. That is, the IBL and the corresponding DBL form a binding partner pair. By "specifically bind" herein is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion-metal ion ligands or chelators pairs are also useful. Antigen-antibody pairs, enzymes and substrates or inhibitors, other protein-protein interacting pairs, receptor-ligands, complementary nucleic acids, and carbohydrates and their binding partners are also suitable binding pairs. Nucleic acid—nucleic acid binding proteins pairs are also useful. Similarly, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target; such an aptamer-target pair can be used as the IBL-DBL pair. Similarly, there is a wide body of literature relating to the development of binding pairs based on combinatorial chemistry methods.

In a preferred embodiment, the IBL is a molecule whose color or luminescence properties change in the presence of a selectively-binding DBL. For example, the IBL may be a fluorescent pH indicator whose emission intensity changes with pH. Similarly, the IBL may be a fluorescent ion indicator, whose emission properties change with ion concentration.

Alternatively, the IBL is a molecule whose color or luminescence properties change in the presence of various solvents. For example, the IBL may be a fluorescent molecule such as an ethidium salt whose fluorescence intensity increases in hydrophobic environments. Similarly, the IBL may be a derivative of fluorescein whose color changes between aqueous and nonpolar solvents.

In one embodiment, the DBL may be attached to a bead, i.e. a "decoder bead", that may carry a label such as a fluorophore.

In a preferred embodiment, the IBL-DBL pair comprise substantially complementary single-stranded nucleic acids. In this embodiment, the binding ligands can be referred to as "identifier probes" and "decoder probes". Generally, the identifier and decoder probes range from about 4 basepairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

In a preferred embodiment, the microspheres do not contain an optical signature. That is, as outlined in PCT US98105025, PCT/US99/20914, U.S. Pat. No. 6,023,540 and U.S. Ser. Nos. 09/151,877 and 09/450,829, each subpopulation of microspheres may comprise a unique optical signature or optical tag that is used to identify the unique bioactive agent of that subpopulation of microspheres; that is, decoding utilizes optical properties of the beads such that a bead comprising the unique optical signature may be distinguished from beads at other locations with different optical signatures. This assigns each bioactive agent a unique optical signature such that any microspheres comprising that bioactive agent are identifiable on the basis of the signature. These optical signatures comprised dyes, usually chromophores or fluorophores, that were entrapped or attached to the beads themselves. Diversity of optical signatures utilized different fluorochromes, different ratios of mixtures of fluorochromes, and different concentrations (intensities) of fluorochromes.

In a preferred embodiment, the arrays do rely solely on the use of optical properties to decode the arrays. However, as will be appreciated by those in the art, it is possible in some embodiments to utilize optical signatures as an additional coding method, in conjunction with the other methods outlined below. Thus, for example, as is more fully outlined below, the size of the array may be effectively increased while using a single set of decoding moieties in several ways, one of which is the use of optical signatures one some beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different IBLs. By using a plurality of different IBLs to encode each bioactive agent, the number of possible unique codes is substantially increased. That is, by using one unique IBL per bioactive agent, the size of the array will be the number of unique IBLs (assuming no "reuse" occurs, as outlined below). However, by using a plurality of different IBLs per bead, n, the size of the array can be increased to r, when the presence or absence of each IBL is used as the indicator. For example, the assignment of 10 IBLs per bead generates a 10 bit binary code, where each bit can be designated as "1" (IBL is present) or "0" (IBL is absent). A 10 bit binary code has $2^{10}$ possible variants. However, as is more fully discussed below, the size of the array may be further increased if another parameter is included such as concentration or intensity; thus for example, if two different concentrations of the IBL are used, then the array size increases as $3^n$. Thus, in this embodiment, each individual bioactive agent in the array is assigned a combination of IBLs, which can be added to the beads prior to the addition of the bioactive agent, after, or during the synthesis of the bioactive agent, i.e. simultaneous addition of IBLs and bioactive agent components.

Alternatively, when the bioactive agent is a polymer of different residues, i.e. when the bioactive agent is a protein or nucleic acid, the combination of different IBLs can be used to elucidate the sequence of the protein or nucleic acid.

Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

The system is similar for proteins but requires a larger number of different IBLs to identify each position, depending on the allowed diversity at each position. Thus for example, if every amino acid is allowed at every position, five different IBLs are required for each position. However, as outlined above, for example when using random peptides as the bioactive agents, there may be bias built into the system; not all amino acids may be present at all positions, and some positions may be preset; accordingly, it may be possible to utilize four different IBLs for each amino acid.

In this way, a sort of "bar code" for each sequence can be constructed; the presence or absence of each distinct IBL will allow the identification of each bioactive agent.

In addition, the use of different concentrations or densities of IBLs allows a "reuse" of sorts. If, for example, the bead comprising a first agent has a 1× concentration of IBL, and a second bead comprising a second agent has a 10× concentration of IBL, using saturating concentrations of the corresponding labelled DBL allows the user to distinguish between the two beads.

Once the microspheres comprising the candidate agents and the unique tags are generated, they are added to the substrate to form an array. In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads removed.

In one embodiment the beads or microspheres are contacted with or distributed on the array through the microfluidic channels. That is, the beads flow through the channels and are allowed to settle into the wells of the substrate. Beads can be distributed onto the array either prior to or subsequent to their contacting the sample. A preferred embodiment utilizes contacting the beads and the sample prior to loading the array, coupled with mixing, as this can increase the kinetics of binding. When the beads are contacted with the sample prior to distribution, the solution may be "emptied" into a microwell array. That is the sample including the beads flows into a channel or detection well that comprises microwells. The beads settle into the wells and excess sample is removed.

In one embodiment the invention provides a method of loading beads into an array. In a preferred embodiment the invention provides a method for increasing the filling efficiency of beads on an array. The array may contain wells as described herein. In one embodiment the invention includes the combination of microfluidics and fluid flow, including electroosmotic flow, with microsphere arrays. Benefits associated with using microfluidics to perform bead loading include: 1) overall volumes employed are drastically reduced which in turn reduces the number of beads that need to be synthesized; 2) microchannels can be made to exactly match the size of the array, thus serving to deliver the beads in a more efficient, focused manner with minimal wastage.

In a first embodiment, an array is incorporated into a bead delivery channel, i.e. a microchannel, according to one of several methods. The bead delivery channel may be microfabricated. Most simply, the array, which is preferably a microwell array, is embossed or molded directly into the floor at one or more defined locations throughout the microchannel. In a preferred embodiment the microchannel and array are formed from plastic (which includes a wide scope of polymeric materials), although the device could also be micromachined into other materials such as silicon or glass, for example. The array could also be fabricated separately such as in the case of a fiber-optic bundle. The array could then be mated to the microfluidics through microcouplers or press fits through a port in the side wall of a plastic microfluidic part, for example.

Figure 2:
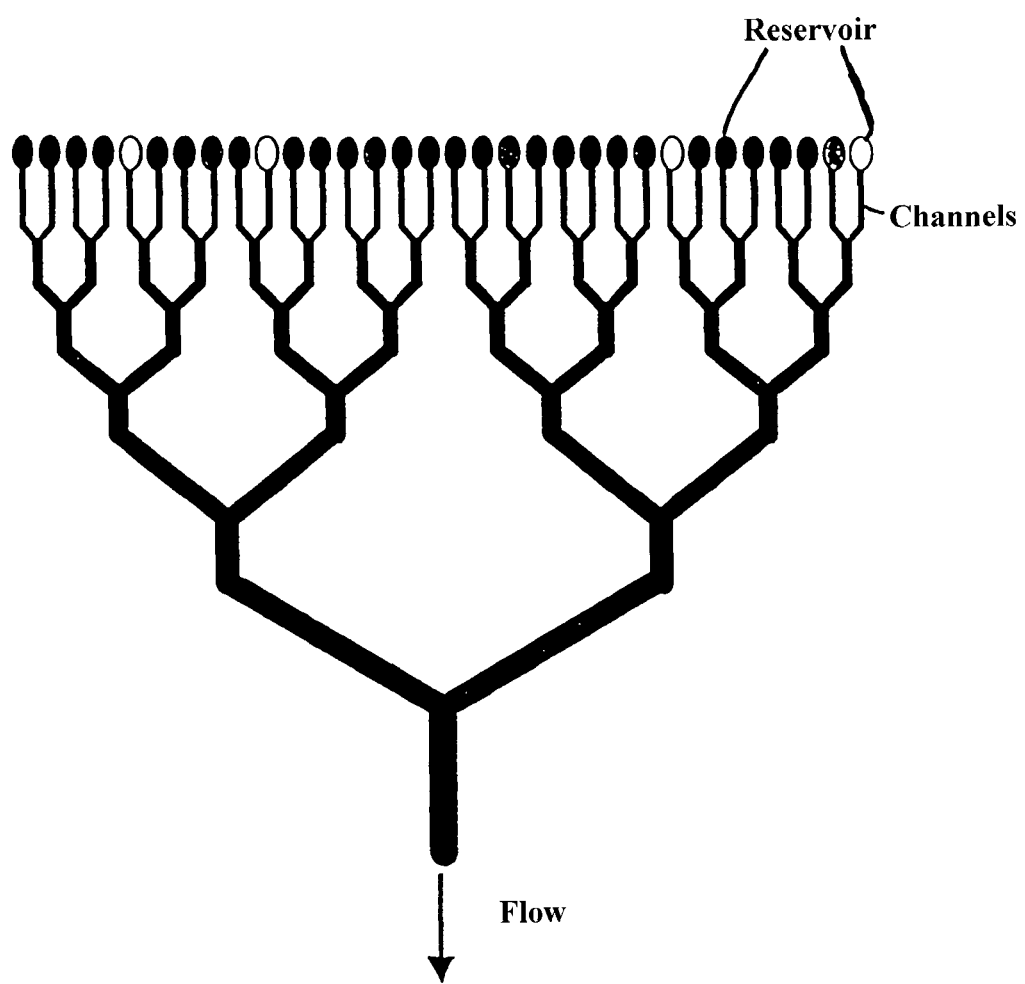
FIG. 2 depicts a microchannel tree structure for on-chip bead distribution. Each reservoir can be filled with a different bead solution.

In addition, a particular bead population of interest is introduced into the microwell array. Although the bead mixture can be prepared ahead of time manually or with the aid of a robotic dispenser, in some embodiments it is preferable to build the bead mixture on-chip, i.e. on the array. The use of microfluidics has the advantage of handling extremely small volumes of solutions with very tight control over these volumes. Accordingly, the invention provides improved bead mixing (i.e. more even representation of each bead type in the final mixture) by exploiting these advantages. In one embodiment improved bead mixing is accomplished by using a microchannel tree structure upstream from the array (see FIG. 2), containing multiple inlets which gradually converge into a single channel. That is, a plurality of channels converge into a common chamber or module. This chamber or module may be a detection chamber or module. Alternatively, it may be a chamber for processing, or preparing the beads.

In some embodiments, reservoirs are present at the mouth of each channel where the different bead solutions reside. The bead solutions may be either manually pipetted or, preferably, robotically dispensed. In a preferred embodiment, the volume in the reservoir is several times larger than the amount of solution to be drawn into the channel. As such, the uniformity of the final bead pool is not limited by the degree to which one can uniformly pipette or dispense samples into the channels. Rather the invention provides the advantage of drawing precise amounts of suspension, for example, electrokinetically, from each reservoir. The bead suspensions continue to converge until one mixture is obtained in the final channel structure.

In additional embodiments, other methods of moving the beads through the channels could be used, such as capillary action, electrostatic forces, centrifugal force, or simply gravity. In addition, if it was desired to have beads present in a mixture in specific unequal amounts, the number of channels devoted to any given bead type could be varied. Alternatively, channels could be made of different lengths or thicknesses in order to effect desired changes in final concentration of a particular starting bead type. Also, the structure could be designed with far more (or less) complexity and multiplexing, depending on the pooling needs.

Figure 3:
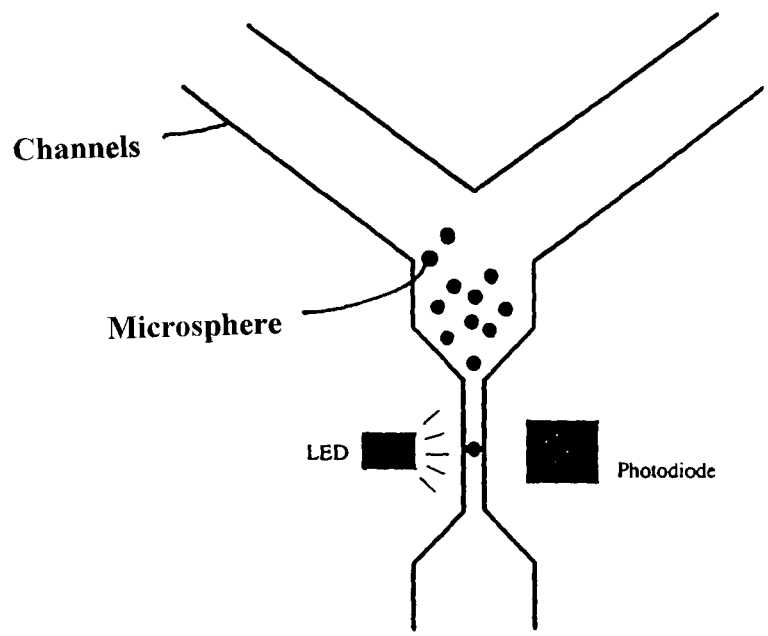
FIG. 3 depicts a configuration of a bead-counting region built into a channel of a tree structure or network.

In an additional embodiment, for even more precise control over mixing a bead counting device is incorporated into the microchannel mixer. In this embodiment each reservoir is triggered successively to flow, i.e. distribute beads, through the network. The beads are counted before the next bead type is injected. This allows for precise control over exactly how many beads of each type are present in the final mixture. In some embodiments, the beads are then distributed into a final "holding reservoir" until all bead types were present in the mixture. In an additional embodiment, one could use voltage displacement measurements (Courter principle) or light scattering methods, and build a narrow region into the device that allows only single beads to pass by the counting region at a time (see, for example FIG. 3).

Figure 4:
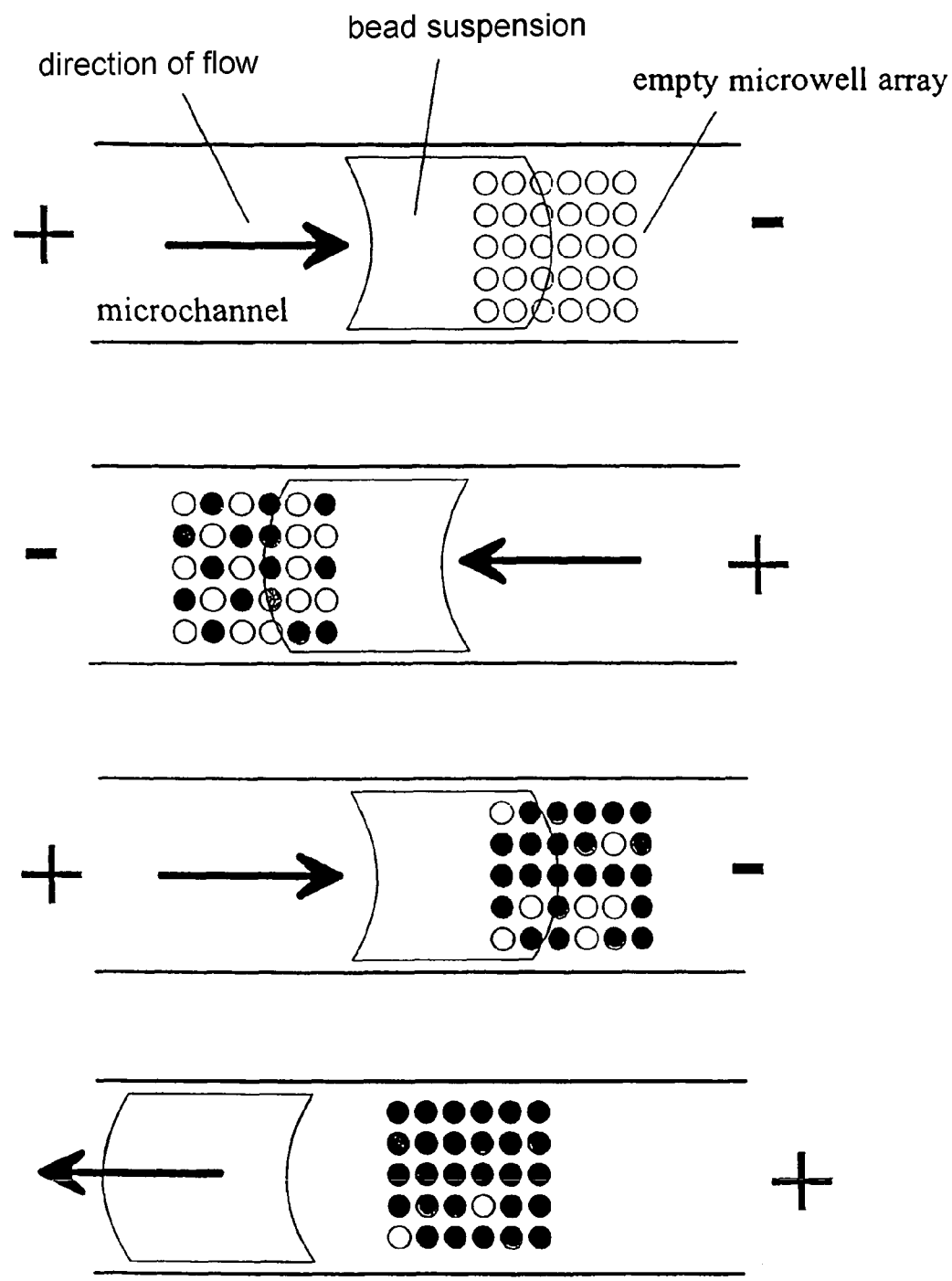
FIG. 4 depicts bead loading by sequentially reversing the direction of flow over the microarray until the wells are filled.

In an additional embodiment, the present invention provides an alternative approach. Using microchannels and fluid flow, such as electroosmotic flow, in conjunction with the array, a defined quantity of beads or a bead mixture is delivered to the array region and then the direction of the bead flow is repeatedly reversed over the array until every well or substantially every well is filled. When electroosmotic pumping is used, the method includes alternately changing the potentials at either end of the microchannel in a continuous fashion. Other methods of reversing fluid flos can be used depending on the kind of pumping being used. This results in the formation of a type of sifter with no moving mechanical parts (see, for example, FIG. 4). The repeated back-and-forth motion of the bead suspension also promotes the immobilization of only the best-suited (size or otherwise) microspheres to create a highly stable array. In addition the invention includes the formation of charge cross-sections in the channel that promote the travel of beads along the floor such that their interaction with the wells is enhanced.

In an alternative embodiment, the beads are applied to or distributed onto the array, including fiber optic bundles, prior to combining the array with the microfluidic chip.

It should be noted that not all sites of an array may comprise a bead; that is, there may be some sites on the substrate surface which are empty. In addition, there may be some sites that contain more than one bead, although this is generally not preferred.

In some embodiments, for example when chemical attachment is done, it is possible to attach the beads in a non-random or ordered way. For example, using photoactivatible attachment linkers or photoactivatible adhesives or masks, selected sites on the array may be sequentially rendered suitable for attachment, such that defined populations of beads are laid down.

The arrays of the present invention are constructed such that information about the identity of the candidate agent is built into the array, such that the random deposition of the beads in the fiber wells can be "decoded" to allow identification of the candidate agent at all positions. This may be done in a variety of ways, and either before, during or after the use of the array to detect target molecules, as is outlined in U.S. Ser. Nos. 60/090,473, 09/189,543, 09/344,526 and 60/172, 106 and PCT/US99/14387, all of which are expressly incorporated herein by reference.

Thus, after the array is made, it is "decoded" in order to identify the location of one or more of the bioactive agents, i.e. each subpopulation of beads, on the substrate surface.

In a preferred embodiment, a selective decoding system is used. In this case, only those microspheres exhibiting a change in the optical signal as a result of the binding of a target analyte are decoded. This is commonly done when the number of "hits", i.e. the number of sites to decode, is generally low. That is, the array is first scanned under experimental conditions in the absence of the target analytes. The sample containing the target analytes is added, and only those locations exhibiting a change in the optical signal are decoded. For example, the beads at either the positive or negative signal locations may be either selectively tagged or released from the array (for example through the use of photocleavable linkers), and subsequently sorted or enriched in a fluorescence-activated cell sorter (FACS). That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags mass spectral tags.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead contains a fluorescent dye. After the assay and the identification of the "positives" or "active beads", light is shown down either only the positive fibers or only the negative fibers, generally in the presence of a light-activated reagent (typically dissolved oxygen). In the former case, all the active beads are photobleached. Thus, upon non-selective release of all the beads with subsequent sorting, for example using a fluorescence activated cell sorter (FACS) machine, the non-fluorescent active beads can be sorted from the fluorescent negative beads. Alternatively, when light is shown down the negative fibers, all the negatives are non-fluorescent and the postives are fluorescent, and sorting can proceed. The characterization of the attached bioactive agent may be done directly, for example using mass spectroscopy.

Alternatively, the identification may occur through the use of identifier moieties ("IMs"), which are similar to IBLs but need not necessarily bind to DBLs. That is, rather than elucidate the structure of the bioactive agent directly, the composition of the IMs may serve as the identifier. Thus, for example, a specific combination of IMs can serve to code the bead, and be used to identify the agent on the bead upon release from the bead followed by subsequent analysis, for example using a gas chromatograph or mass spectroscope.

Alternatively, rather than having each bead contain a fluorescent dye, each bead comprises a non-fluorescent precursor to a fluorescent dye. For example, using photocleavable protecting groups, such as certain ortho-nitrobenzyl groups, on a fluorescent molecule, photoactivation of the fluorochrome can be done. After the assay, light is shown down again either the "positive" or the "negative" fibers, to distinguish these populations. The illuminated precursors are then chemically converted to a fluorescent dye. All the beads are then released from the array, with sorting, to form populations of fluorescent and non-fluorescent beads (either the positives and the negatives or vice versa).

In an alternate preferred embodiment, the sites of attachment of the beads (for example the wells) include a photopolymerizable reagent, or the photopolymerizable agent is added to the assembled array. After the test assay is run, light is shown down again either the "positive" or the "negative" fibers, to distinguish these populations. As a result of the irradiation, either all the positives or all the negatives are polymerized and trapped or bound to the sites, while the other population of beads can be released from the array.

In a preferred embodiment, the location of every bioactive agent is determined using decoder binding ligands (DBLs).

As outlined above, DBLs are binding ligands that will either bind to identifier binding ligands, if present, or to the bioactive agents themselves, preferably when the bioactive agent is a nucleic acid or protein.

In a preferred embodiment, as outlined above, the DBL binds to the IBL.

In a preferred embodiment, the bioactive agents are single-stranded nucleic acids and the DBL is a substantially complementary single-stranded nucleic acid that binds (hybridizes) to the bioactive agent, termed a decoder probe herein. A decoder probe that is substantially complementary to each candidate probe is made and used to decode the array. In this embodiment, the candidate probes and the decoder probes should be of sufficient length (and the decoding step run under suitable conditions) to allow specificity; i.e. each candidate probe binds to its corresponding decoder probe with sufficient specificity to allow the distinction of each candidate probe.

In a preferred embodiment, the DBLs are either directly or indirectly labeled. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include luminescent labels, including fluorochromes. In a preferred embodiment, the DBL is directly labeled, that is, the DBL comprises a label. In an alternate embodiment, the DBL is indirectly labeled; that is, a labeling binding ligand (LBL) that will bind to the DBL is used. In this embodiment, the labeling binding ligand-DBL pair can be as described above for IBL-DBL pairs.

Accordingly, the identification of the location of the individual beads (or subpopulations of beads) is done using one or more decoding steps comprising a binding between the labeled DBL and either the IBL or the bioactive agent (i.e. a hybridization between the candidate probe and the decoder probe when the bioactive agent is a nucleic acid). After decoding, the DBLs can be removed and the array can be used; however, in some circumstances, for example when the DBL binds to an IBL and not to the bioactive agent, the removal of the DBL is not required (although it may be desirable in some circumstances). In addition, as outlined herein, decoding may be done either before the array is used to in an assay, during the assay, or after the assay.

In one embodiment, a single decoding step is done. In this embodiment, each DBL is labeled with a unique label, such that the number of unique tags is equal to or greater than the number of bioactive agents (although in some cases, "reuse" of the unique labels can be done, as described herein; similarly, minor variants of candidate probes can share the same decoder, if the variants are encoded in another dimension, i.e. in the bead size or label). For each bioactive agent or IBL, a DBL is made that will specifically bind to it and contains a unique tag, for example one or more fluorochromes. Thus, the identity of each DBL, both its composition (i.e. its sequence when it is a nucleic acid) and its label, is known. Then, by adding the DBLs to the array containing the bioactive agents under conditions which allow the formation of complexes (termed hybridization complexes when the components are nucleic acids) between the DBLs and either the bioactive agents or the IBLs, the location of each DBL can be elucidated. This allows the identification of the location of each bioactive agent; the random array has been decoded. The DBLs can then be removed, if necessary, and the target sample applied.

In a preferred embodiment, the number of unique labels is less than the number of unique bioactive agents, and thus a sequential series of decoding steps are used. To facilitate the discussion, this embodiment is explained for nucleic acids, although other types of bioactive agents and DBLs are useful as well. In this embodiment, decoder probes are divided into n sets for decoding. The number of sets corresponds to the number of unique tags. Each decoder probe is labeled in n separate reactions with n distinct tags. All the decoder probes share the same n tags. The decoder probes are pooled so that each pool contains only one of the n tag versions of each decoder, and no two decoder probes have the same sequence of tags across all the pools. The number of pools required for this to be true is determined by the number of decoder probes and the n. Hybridization of each pool to the array generates a signal at every address. The sequential hybridization of each pool in turn will generate a unique, sequence-specific code for each candidate probe. This identifies the candidate probe at each address in the array. For example, if four tags are used, then 4×n sequential hybridizations can ideally distinguish $4^n$ sequences, although in some cases more steps may be required. After the hybridization of each pool, the hybrids are denatured and the decoder probes removed, so that the probes are rendered single-stranded for the next hybridization (although it is also possible to hybridize limiting amounts of target so that the available probe is not saturated. Sequential hybridizations can be carried out and analyzed by subtracting pre-existing signal from the previous hybridization).

An example is illustrative. Assuming an array of 16 probe nucleic acids (numbers 1-16), and four unique tags (four different fluors, for example; labels A-D). Decoder probes 1-16 are made that correspond to the probes on the beads. The first step is to label decoder probes 1-4 with tag A, decoder probes 5-8 with tag B, decoder probes 9-12 with tag C, and decoder probes 13-16 with tag D. The probes are mixed and the pool is contacted with the array containing the beads with the attached candidate probes. The location of each tag (and thus each decoder and candidate probe pair) is then determined. The first set of decoder probes are then removed. A second set is added, but this time, decoder probes 1, 5, 9 and 13 are labeled with tag A, decoder probes 2, 6, 10 and 14 are labeled with tag B, decoder probes 3, 7, 11 and 15 are labeled with tag C, and decoder probes 4, 8, 12 and 16 are labeled with tag D. Thus, those beads that contained tag A in both decoding steps contain candidate probe 1; tag A in the first decoding step and tag B in the second decoding step contain candidate probe 2; tag A in the first decoding step and tag C in the second step contain candidate probe 3; etc.

In one embodiment, the decoder probes are labeled in situ; that is, they need not be labeled prior to the decoding reaction. In this embodiment, the incoming decoder probe is shorter than the candidate probe, creating a 5' "overhang" on the decoding probe. The addition of labeled ddNTPs (each labeled with a unique tag) and a polymerase will allow the addition of the tags in a sequence specific manner, thus creating a sequence-specific pattern of signals. Similarly, other modifications can be done, including ligation, etc.

In addition, since the size of the array will be set by the number of unique decoding binding ligands, it is possible to "reuse" a set of unique DBLs to allow for a greater number of test sites. This may be done in several ways; for example, by using some subpopulations that comprise optical signatures. Similarly, the use of a positional coding scheme within an array; different sub-bundles may reuse the set of DBLs. Similarly, one embodiment utilizes bead size as a coding modality, thus allowing the reuse of the set of unique DBLs for each bead size. Alternatively, sequential partial loading of arrays with beads can also allow the reuse of DBLs. Furthermore, "code sharing" can occur as well.

In a preferred embodiment, the DBLs may be reused by having some subpopulations of beads comprise optical signatures. In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique optical signatures may be generated. This may be done by covalently attaching the dyes to the surface of the beads, or alternatively, by entrapping the dye within the bead. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, and others described in the 6th Edition of the Molecular Probes Handbook by Richard P. Haugland, hereby expressly incorporated by reference.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the pores of the beads.

Additionally, encoding in the ratios of the two or more dyes, rather than single dye concentrations, is preferred since it provides insensitivity to the intensity of light used to interrogate the reporter dye's signature and detector sensitivity.

In a preferred embodiment, a spatial or positional coding system is done. In this embodiment, there are sub-bundles or subarrays (i.e. portions of the total array) that are utilized. By analogy with the telephone system, each subarray is an "area code", that can have the same tags (i.e. telephone numbers) of other subarrays, that are separated by virtue of the location of the subarray. Thus, for example, the same unique tags can be reused from bundle to bundle. Thus, the use of 50 unique tags in combination with 100 different subarrays can form an array of 5000 different bioactive agents. In this embodiment, it becomes important to be able to identify one bundle from another; in general, this is done either manually or through the use of marker beads, i.e. beads containing unique tags for each subarray.

In alternative embodiments, additional encoding parameters can be added, such as microsphere size. For example, the use of different size beads may also allow the reuse of sets of DBLs; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different bioactive agent (or the subpopulations each comprise a different bioactive agent), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each bioactive agent is determined, generally through the use of DBLs. The second sublibrary is then added, and the location of each bioactive agent is again determined. The signal in this case will comprise the signal from the "first" DBL and the "second" DBL; by comparing the two matrices the location of each bead in each sublibrary can be determined. Similarly, adding the third, fourth, etc. sublibraries sequentially will allow the array to be filled.

In a preferred embodiment, codes can be "shared" in several ways. In a first embodiment, a single code (i.e. IBL/DBL pair) can be assigned to two or more agents if the target analytes different sufficiently in their binding strengths. For example, two nucleic acid probes used in an mRNA quantitation assay can share the same code if the ranges of their hybridization signal intensities do not overlap. This can occur, for example, when one of the target sequences is always present at a much higher concentration than the other. Alternatively, the two target sequences might always be present at a similar concentration, but differ in hybridization efficiency.

Alternatively, a single code can be assigned to multiple agents if the agents are functionally equivalent. For example, if a set of oligonucleotide probes are designed with the common purpose of detecting the presence of a particular gene, then the probes are functionally equivalent, even though they may differ in sequence. Similarly, if classes of analytes are desired, all probes for different members of a class such as kinases or G-protein coupled receptors could share a code. Similarly, an array of this type could be used to detect homologs of known genes. In this embodiment, each gene is represented by a heterologous set of probes, hybridizing to different regions of the gene (and therefore differing in sequence). The set of probes share a common code. If a homolog is present, it might hybridize to some but not all of the probes. The level of homology might be indicated by the fraction of probes hybridizing, as well as the average hybridization intensity. Similarly, multiple antibodies to the same protein could all share the same code.

As will be appreciated by those in the art, the decoding may be done prior to the placement of the detection module in the microfluidic device, or afterwards.

Once made, the compositions of the invention find use in a number of applications. In a preferred embodiment, the compositions are used to probe a sample solution for the presence or absence of a target analyte, including the quantification of the amount of target analyte present, as defined above.

In a preferred embodiment, the target analyte is a nucleic acid. These assays find use in a wide variety of applications.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, cytochrome p450s or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, chlamydia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

The present invention also finds use as a methodology for the detection of mutations or mismatches in target nucleic acid sequences. For example, recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Cordor et al., Science 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998). The compositions of the present invention may easily be substituted for the arrays of the prior art.

In a preferred embodiment, the compositions of the invention are used to screen bioactive agents to find an agent that will bind, and preferably modify the function of, a target molecule. As above, a wide variety of different assay formats may be run, as will be appreciated by those in the art. Generally, the target analyte for which a binding partner is desired is labeled; binding of the target analyte by the bioactive agent results in the recruitment of the label to the bead, with subsequent detection.

Generally, a sample containing a target analyte (whether for detection of the target analyte or screening for binding partners of the target analyte) is added to the array, under conditions suitable for binding of the target analyte to at least one of the bioactive agents, i.e. generally physiological conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optical interrogatable event.

In a preferred embodiment, the change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorochromes, for example during PCR amplification as is known in the art. Alternatively, upon binding of the target sequences, a hybridization indicator may be used as the label. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, only in the presence of target hybridization will the label light up. Thus, upon binding of the target analyte to a bioactive agent, there is a new optical signal generated at that site, which then may be detected.

Alternatively, in some cases, as discussed above, the target analyte such as an enzyme generates a species that is either directly or indirectly optical detectable.

Furthermore, in some embodiments, a change in the optical signature may be the basis of the optical signal. For example, the interaction of some chemical target analytes with some fluorescent dyes on the beads may alter the optical signature, thus generating a different optical signal.

As will be appreciated by those in the art, in some embodiments, the presence or absence of the target analyte may be done using changes in other optical or non-optical signals, including, but not limited to, surface enhanced Raman spectroscopy, surface plasmon resonance, radioactivity, etc.

The assays may be run under a variety of experimental conditions, as will be appreciated by those in the art. A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

In a preferred embodiment, two-color competitive hybridization assays are run. These assays can be based on traditional sandwich assays. The beads contain a capture sequence located on one side (upstream or downstream) of the SNP, to capture the target sequence. Two SNP allele-specific probes, each labeled with a different fluorophor, are hybridized to the target sequence. The genotype can be obtained from a ratio of the two signals, with the correct sequence generally exhibiting better binding. This has an advantage in that the target sequence itself need not be labeled. In addition, since the probes are competing, this means that the conditions for binding need not be optimized. Under conditions where a mismatched probe would be stably bound, a matched probe can still displace it. Therefore the competitive assay can provide better discrimination under those conditions. Because many assays are carried out in parallel, conditions cannot be optimzed for every probe simultaneously. Therefore, a competitive assay system can be used to help compensate for non-optimal conditons for mismatch discrimination.

In a preferred embodiment, dideoxynucleotide chain-termination sequencing is done using the compositions of the invention. In this embodiment, a DNA polymerase is used to extend a primer using fluorescently labeled ddNTPs. The 3' end of the primer is located adjacent to the SNP site. In this way, the single base extension is complementary to the sequence at the SNP site. By using four different fluorophors, one for each base, the sequence of the SNP can be deduced by comparing the four base-specific signals. This may be done in several ways. In a first embodiment, the capture probe can be extended; in this approach, the probe must either be synthesized 5'-3' on the bead, or attached at the 5' end, to provide a free 3' end for polymerase extension. Alternatively, a sandwich type assay can be used; in this embodiment, the target is captured on the bead by a probe, then a primer is annealed and extended. Again, in the latter case, the target sequence need not be labeled. In addition, since sandwich assays require two specific interactions, this provides increased stringency which is particularly helpful for the analysis of complex samples.

SNP analysis may also be done using pyrosequencing and other methods, as is generally described in U.S. Ser. Nos. 60/130,089, 60/160,027, 09/513,362, 60/135,051, 60/161, 148, 09/517,945, 60/135,053, 09/425,633, 09/535,854, 09/553, 993 and 09/556,463, and PCT application entitled "Detection of Nucleic Acid Reactions on Bead Arrays" filed Apr. 20, 2000 (no serial number received) expressly incorporated herein by reference.

In some embodiments, the use of adapters as described in U.S. Ser. Nos. 60/135,123 and 60/160,917,both of which are expressly incorporated herein by reference, finds use in the invention.

In addition, when the target analyte and the DBL both bind to the agent, it is also possible to do detection of non-labeled target analytes via competition of decoding.

In a preferred embodiment, the methods of the invention are useful in array quality control. Prior to this invention, no methods have been described that provide a positive test of the performance of every probe on every array. Decoding of the array not only provides this test, it also does so by making use of the data generated during the decoding process itself. Therefore, no additional experimental work is required. The invention requires only a set of data analysis algorithms that can be encoded in software.

The quality control procedure can identify a wide variety of systematic and random problems in an array. For example, random specks of dust or other contaminants might cause some sensors to give an incorrect signal-this can be detected during decoding. The omission of one or more agents from multiple arrays can also be detected. An advantage of this quality control procedure is that it can be implemented immediated prior to the assay itself, and is a true functional test of each individual sensor. Therefore any problems that might occur between array assembly and actual use can be detected. In applications where a very high level of confidence is required, and/or there is a significant chance of sensor failure during the experimental procedure, decoding and quality control can be conducted both before and after the actual sample analysis.

In a preferred embodiment, the arrays can be used to do reagent quality control. In many instances, biological macromolecules are used as reagents and must be quality controlled. For example, large sets of oligonucleotide probes may be provided as reagents. It is typically difficult to perform quality control on large numbers of different biological macromolecules. The approach described here can be used to do this by treating the reagents (formulated as the DBLs) as variable instead of the arrays.

In a preferred embodiment, the methods outlined herein are used in array calibration. For many applications, such as mRNA quantitation, it is desirable to have a signal that is a linear response to the concentration of the target analyte, or, alternatively, if non-linear, to determine a relationship between concentration and signal, so that the concentration of the target analyte can be estimated. Accordingly, the present invention provides methods of creating calibration curves in parallel for multiple beads in an array. The calibration curves can be created under conditions that simulate the complexity of the sample to be analyzed. Each curve can be constructed independently of the others (e.g. for a different range of concentrations), but at the same time as all the other curves for the array. Thus, in this embodiment, the sequential decoding scheme is implemented with different concentrations being used as the code "labels", rather than different fluorophores. In this way, signal as a response to concentration can be measured for each bead. This calibration can be carried out just prior to array use, so that every probe on every array is individually calibrated as needed.

In a preferred embodiment, the methods of the invention can be used in assay development as well. Thus, for example, the methods allow the identification of good and bad probes; as is understood by those in the art, some probes do not function well because they do not hybridize well, or because they cross-hybridize with more than one sequence. These problems are easily detected during decoding. The ability to rapidly assess probe performance has the potential to greatly reduce the time and expense of assay development.

Similarly, in a preferred embodiment, the methods of the invention are useful in quantitation in assay development. Major challenges of many assays is the ability to detect differences in analyte concentrations between samples, the ability to quantitate these differences, and to measure absolute concentrations of analytes, all in the presence of a complex mixture of related analytes. An example of this problem is the quantitation of a specific mRNA in the presence of total cellular mRNA. One approach that has been developed as a basis of mRNA quantitation makes use of a multiple match and mismatch probe pairs (Lockhart et al., 1996), hereby incorporated by reference in its entirety. While this approach is simple, it requires relatively large numbers of probes. In this approach, a quantitative response to concentration is obtained by averaging the signals from a set of different probes to the gene or sequence of interest. This is necessary because only some probes respond quantitatively, and it is not possible to predict these probes with certainty. In the absence of prior knowledge, only the average response of an appropriately chosen collection of probes is quantitative. However, in the present invention, this can be applied generally to nucleic acid based assays as well as other assays. In essence, the approach is to identify the probes that respond quantitatively in a particular assay, rather than average them with other probes. This is done using the array calibration scheme outlined above, in which concentration-based codes are used. Advantages of this approach include: fewer probes are needed; the accuracy of the measurement is less dependent on the number of probes used; and that the response of the sensors is known with a high level of certainty, since each and every sequence can be tested in an efficient manner. It is important to note that probes that perform well are chosen empirically, which avpids the difficulties and uncertainties of predicting probe performance, particularly in complex sequence mixtures. In contrast, in experiments described to date with ordered arrays, relatively small numbers of sequences are checked by performing quantitative spiking experiments, in which a known mRNA is added to a mixture.

Generally, the methods are as follows. In a preferred embodiment, the target is moved into the detection module. In general, two methods may be employed; the assay complexes as described below are formed first (i.e. all the soluble components are added together, either simultaneously or sequentially), "upstream" of the detection module, and then the complex is added to the surface for subsequent binding to a detection array. Alternatively, the target may be added where it binds the capture binding ligand and then additional components are added. The latter is described in detail below, but either procedure may be followed. Similarly, some components may be added, electrophoresed, and other components added; for example, the target analyte may be combined with any capture extender probes and then transported, etc. In addition, as outlined herein, "washing" steps may be done using the introduction of buffer into the detection module, wherein excess reagents (non-bound analytes, excess probes, etc.) can be driven from the surface.

In a preferred embodiment, the methods include processing the sample upstream of the detection chamber. That is, the sample processing occurs in one or more channels or chambers of the chip. In one embodiment, sample preparation occurs in more than one channel; however, sample processing occurs in parallel. The prepared sample is then recombined into a single channel that flows to the detection module. Thus, for example, a variety of different PCR reactions may be done in a plurality of chambers, with all the reaction products being added to a single array. Alternatively, parallel reactions can be added to different arrays. In a preferred embodiment, the reactions happen sequentially; for example, a first PCR reaction can be performed in a first chamber and a "nested" PCR reaction performed in a subsequent chamber.

Sample movement within the channels can occur through conventional methods including electro-osmotic flow, capillary action or pressure, as outlined herein, and includes the use of "on chip" and "off chip" pumps. In one embodiment, movement of the sample stops once the sample contacts the detection module. This allows time for any of the above-described assays to occur. Alternatively, movement is not necessarily stopped, but rather slows down as the sample crosses the array. Alternatively, for fast reactions or when recirculation is used, the flow is unchanged.

Regulating sample flow is accomplished by reducing the driving force that is applied to the sample. Alternatively, physical aspects of the detection module can be altered to affect sample flow. In one embodiment the diameter of the detection module is increased relative to other channels. This results in slowing the sample flow.

In an alternative embodiment, sample flow can be re-circulated across the detection module. In this embodiment, a closed looped channel is used to re-circulate the sample. Recirculation also may improve the assay and/or signal detection by facilitating mixing across the array.

The sample is introduced to the array in the detection module, and then immobilized or attached to the beads. In one embodiment, this is done by forming an attachment complex (frequently referred to herein as a hybridization complex when nucleic acid components are used) between a capture probe and a portion of the target analyte. Alternatively, the attachment of the target sequence to the beads is done simultaneously with the other reactions.

The method proceeds with the introduction of amplifier probes, if utilized. In a preferred embodiment, the amplifier probe comprises a first probe sequence that is substantially complementary to a portion of the target sequence, and at least one amplification sequence.

In one embodiment, the first probe sequence of the amplifier probe is hybridized to the target sequence, and any unhybridized amplifier probe is removed. This will generally be done as is known in the art, and depends on the type of assay. When the target sequence is immobilized on the array surface, the removal of excess reagents generally is done via one or more washing steps, as will be appreciated by those in the art.

The invention thus provides assay complexes that minimally comprise a target sequence and a label probe. "Assay complex" herein is meant the collection of attachment or hybridization complexes comprising analytes, including binding ligands and targets, that allows detection. The composition of the assay complex depends on the use of the different probe component outlined herein. The assay complexes may include the target sequence, label probes, capture extender probes, label extender probes, and amplifier probes, as outlined herein, depending on the configuration used.

The assays are generally run under stringency conditions which allows formation of the label probe attachment complex only in the presence of target. Stringency can be controlled by altering a step parameter that is a thermodynamic variable, including, but not limited to, temperature, formamide concentration, salt concentration, chaotropic salt concentration pH, organic solvent concentration, etc. Stringency may also include the use of an electrophoretic step to drive non-specific (i.e. low stringency) materials away from the detection array.

These parameters may also be used to control non-specific binding, as is generally outlined in U.S. Pat. No. 5,681,697. Thus it may be desirable to perform certain steps at higher stringency conditions; for example, when an initial hybridization step is done between the target sequence and the label extender and capture extender probes. Running this step at conditions which favor specific binding can allow the reduction of non-specific binding.

Once the assay complexes are formed on the detection array, detection proceeds, generally through optical detection of fluorescence. Thus, preferred embodiments utilize detection modules that comprise optical windows to allow detection of target analytes.

In a preferred embodiment, mixing of the sample is performed to facilitate signal detection. That is, as demonstrated in FIG. 1, substantial improvement in signals is observed when sample vibration is implemented during an experiment. In one embodiment, this vibration or mixing is caused by vibration of the chip itself. Alternatively, the mixing is caused by continuous sample flow over the array surface. In this embodiment, the flow of the sample over the surface comprising microspheres provides sufficient high aspect ratio features to induce a level of turbulent flow that enhances the interaction of the sample with the beads. In an alternative embodiment, the vertical microstructures or posts as described above serve to disrupt the laminar flow over the beaded surface.

Accordingly, the present invention further provides devices or apparatus for the detection of analytes using the compositions of the invention. As will be appreciated by those in the art, the modules of the invention can be configured in a variety of ways, depending on the number and size of samples, and the number and type of desired manipulations.

In a preferred embodiment, when a fiber optic bundle is used in the detection module, the results from the experiment are read from the end of the bundle not attached to the chip. In this embodiment, this end of the bundle is connected a CCD camera or other scanning instrument as is known in the art. In addition, the results are examined by focusing a confocal scanning instrument onto the end of the fiber bundle that is within the chip.

As outlined herein, the devices of the invention can be used in combination with apparatus for delivering and receiving fluids to and from the devices. The apparatus can include a "nesting site" for placement of the device(s) to hold them in place and for registering inlet and outlet ports, if present. The apparatus may also include pumps ("off chip pumps"), and means for viewing the contents of the devices, including microscopes, cameras (including CCD cameras and scanners), etc. The apparatus may include electrical contacts in the nesting region which mate with contacts integrated into the structure of the chip, to power heating or electrophoresis, for example. The apparatus may be provided with conventional circuitry sensors in communication with sensors in the device for thermal regulation, for example for PCR thermal regulation. The apparatus may also include a computer system comprising a microprocessor for control of the various modules of the system as well as for data analysis.

All references cited herein are incorporated by reference in their entirety.

We claim:

1. A fluidics device comprising:
   a first channel in fluid communication with an inlet;
   a detection module in fluid communication with said first channel, said detection module comprising an array of wells in communication with a tantalum-containing substrate, a population of microspheres comprising at least a first and a second subpopulation, wherein each subpopulation comprises a bioactive agent and wherein said microspheres are distributed in said wells such that not more than one microsphere is present in each of the wells; and
   a second channel in fluid communication with said detection module and an outlet.

2. The fluidics device of claim 1, wherein the bioactive agent comprises a nucleic acid.

3. The fluidics device of claim 2, wherein the nucleic acid comprises a primer.

4. The fluidics device of claim 3, further comprising an enzyme for extension of the primer.

5. The fluidics device of claim 1, wherein the first subpopulation and the second subpopulation of microspheres are different sized microspheres.

6. The fluidics device of claim 1, wherein the tantalum-containing substrate comprises a plurality of flow channels.

7. The fluidics device of claim 6, wherein at least two flow channels are parallel to each other.

8. The fluidics device of claim 1, wherein the tantalum-containing substrate is configured to hold multiple samples.

9. The fluidics device of claim 1, wherein the wells are randomly distributed on the tantalum-containing substrate.

10. The fluidics device of claim 1, wherein the wells are patterned on the tantalum-containing substrate.

11. The fluidics device of claim 1, further comprising a module in fluid communication with said first channel or with said second channel, said module selected from the group consisting of a sample inlet port, sample collection module, cell handling module, separation module, reaction module, fluid pump, fluid valve, heating module; storage module, and mixing chamber.

12. The fluidics device of claim 11, wherein the fluid pump is selected from the group consisting of electroosmotic pump, and electrohydrodynamic pump.

13. The fluidic device of claim 1, wherein the substrate is a chargeable substrate.

14. A fluidics device comprising:
   an inlet in fluid communication a first channel;
   a detection module in fluid communication with said first channel and comprising:
      an array of wells in communication with a tantalum-containing substrate, wherein the wells are configured to hold a single microsphere;
      a population of microspheres comprising at least a first and a second subpopulation, wherein each subpopulation comprises a bioactive agent; and
   a second channel in fluid communication with said detection module and an outlet.

15. The fluidics device of claim 14, wherein the bioactive agent comprises a nucleic acid.

16. The fluidics device of claim 15, wherein the nucleic acid comprises a primer.

17. The fluidics device of claim 16, further comprising an enzyme for extension of the primer.

18. The fluidics device of claim 14, wherein the first subpopulation and the second subpopulation of microspheres are different sized microspheres.

19. The fluidics device of claim 14, wherein the tantalum-containing substrate comprises a plurality of flow channels.

20. The fluidics device of claim 19, wherein at least two flow channels are parallel to each other.

21. The fluidics device of claim 14, wherein the tantalum-containing substrate is configured to hold multiple samples.

22. The fluidics device of claim 14, wherein the wells are randomly distributed on the tantalum-containing substrate.

23. The fluidics device of claim 14, wherein the wells are patterned on the tantalum-containing substrate.

24. The fluidics device of claim 14, further comprising a module in fluid communication with said first channel or with said second channel, said module selected from the group consisting of a sample inlet port, sample collection module, cell handling module, separation module, reaction module, fluid pump, fluid valve, heating module; storage module, and mixing chamber.

25. The fluidics device of claim 24, wherein the fluid pump is selected from the group consisting of electroosmotic pump, and electrohydrodynamic pump.

26. The fluidic device of claim 14, wherein the substrate is a chargeable substrate.

27. A method of sequencing a nucleic acid comprising:
   providing a fluid comprising a target nucleic acid to the inlet of the fluidics device of claim 17; and
   sequencing said target nucleic acid.

28. The method of claim 27, wherein said sequencing comprises detecting an optical signal.

29. The method of claim 27, wherein said sequencing comprises detecting a non-optical signal.

30. A method of detecting an analyte comprising:
   providing a fluid comprising a target analyte to the inlet of the fluidics device of claim 14; and
   detecting the target analyte bound to at least one of said bioactive agents.

31. The method of claim 30, wherein said target analyte comprises a nucleic acid.

32. The method of claim 30, wherein said detecting comprises detecting an optical signal.

33. The method of claim 30, wherein said detecting comprises detecting a non-optical signal.

34. The fluidics device of claim 27, wherein the first subpopulation and the second subpopulation of microspheres are different sized microspheres.

35. The fluidics device of claim 27, wherein the tantalum-containing substrate comprises a plurality of flow channels.

36. The fluidics device of claim 35, wherein at least two flow channels are parallel to each other.

37. The fluidics device of claim 27, wherein the tantalum-containing substrate is configured to hold multiple samples.

38. The fluidics device of claim 27, wherein the wells are randomly distributed on the tantalum-containing substrate.

39. The fluidics device of claim 27, wherein the wells are patterned on the tantalum-containing substrate.

40. The fluidics device of claim 30, wherein the bioactive agent comprises a nucleic acid.

41. The fluidics device of claim 40, wherein the nucleic acid comprises a primer.

42. The fluidics device of claim 41, further comprising an enzyme for extension of the primer.

43. The fluidics device of claim 30, wherein the first subpopulation and the second subpopulation of microspheres are different sized microspheres.

44. The fluidics device of claim 30, wherein the tantalum-containing substrate comprises a plurality of flow channels.

45. The fluidics device of claim 44, wherein at least two flow channels are parallel to each other.

46. The fluidics device of claim 30, wherein the tantalum-containing substrate is configured to hold multiple samples.

47. The fluidics device of claim 30, wherein the wells are randomly distributed on the tantalum-containing substrate.

48. The fluidics device of claim 30, wherein the wells are patterned on the tantalum-containing substrate.

* * * * *

UNITED STATES PATENT AND TRADEMARK OFFICE
CERTIFICATE OF CORRECTION

PATENT NO. : 8,481,268 B2
APPLICATION NO. : 13/299235
DATED : July 9, 2013
INVENTOR(S) : Mark S. Chee et al.

It is certified that error appears in the above-identified patent and that said Letters Patent is hereby corrected as shown below:

In the Claims

At Column 59, Line 16, in Claim 34, change "The fluidics device of" to --The method of--.

At Column 59, Line 19, in Claim 35, change "The fluidics device of" to --The method of--.

At Column 59, Line 22, in Claim 36, change "The fluidics device of" to --The method of--.

At Column 59, Line 24, in Claim 37, change "The fluidics device of" to --The method of--.

At Column 60, Line 1, in Claim 38, change "The fluidics device of" to --The method of--.

At Column 60, Line 3, in Claim 39, change "The fluidics device of" to --The method of--.

At Column 60, Line 5, in Claim 40, change "The fluidics device of" to --The method of--.

At Column 60, Line 7, in Claim 41, change "The fluidics device of" to --The method of--.

At Column 60, Line 9, in Claim 42, change "The fluidics device of" to --The method of--.

At Column 60, Line 11, in Claim 43, change "The fluidics device of" to --The method of--.

At Column 60, Line 14, in Claim 44, change "The fluidics device of" to --The method of--.

At Column 60, Line 16, in Claim 45, change "The fluidics device of" to --The method of--.

At Column 60, Line 18, in Claim 46, change "The fluidics device of" to --The method of--.

At Column 60, Line 20, in Claim 47, change "The fluidics device of" to --The method of--.

At Column 60, Line 22, in Claim 48, change "The fluidics device of" to --The method of--.

Signed and Sealed this
Twenty-fourth Day of September, 2013

Teresa Stanek Rea
*Deputy Director of the United States Patent and Trademark Office*

UNITED STATES PATENT AND TRADEMARK OFFICE
CERTIFICATE OF CORRECTION

Page 1 of 3

PATENT NO. : 8,481,268 B2
APPLICATION NO. : 13/299235
DATED : July 9, 2013
INVENTOR(S) : Mark S. Chee et al.

It is certified that error appears in the above-identified patent and that said Letters Patent is hereby corrected as shown below:

On Title Page 3, at Item (56), Col. 2, under Other Publications, change "Lighthwave" to --Lightwave--.

In the Specification

At Column 1, Line 60, change "5,071531;" to --5,071,531;--.

At Column 2, Line 47, change "hybridiation" to --hybridization--.

At Column 3, Line 27, change "procaryotic" to --prokaryotic--.

At Column 4, Lines 44-45, change "xathanine hypoxathanine," to --xanthine hypoxanthine,--.

At Column 6, Line 25, change "terepthalate" to --terephthalate--.

At Column 6, Line 28, change "molybdeumn" to --molybdenum--.

At Column 6, Line 45, change "5,071531;" to --5,071,531;--.

At Column 9, Line 30, change "HCL," to --HCl,--.

At Column 10, Lines 60-61, change ""aptomers"" to --"aptamers"--.

At Column 11, Line 14, change "$10^4$" to --$10^{-7}$--.

At Column 12, Line 2, change "disippated" to --dissipated--.

At Column 14, Line 34, change "2d" to --2nd--.

At Column 15, Line 62, change "subtration"," to --subtraction",--.

At Column 16, Line 44, change "2' deoxyadenosine" to --2'-deoxyadenosine--.

Signed and Sealed this
Thirty-first Day of December, 2013

Margaret A. Focarino
*Commissioner for Patents of the United States Patent and Trademark Office*

CERTIFICATE OF CORRECTION (continued)
U.S. Pat. No. 8,481,268 B2

At Column 16, Line 46, change "adn" to --and--.

At Column 16, Line 63, change "HindIII," to --HindII,--.

At Column 17, Line 4, change "iniate" to --initiate--.

At Column 18, Line 10, change "myloblastosis" to --meloblastosis--.

At Column 18, Line 57, change "ϕ1," to --ϕII,--.

At Column 18, Line 58, change "Pseudomonase" to --Pseudomonas--.

At Column 21, Line 22, change "delection)," to --deletion),--.

At Column 22, Line 33, change "expressly" to --expressly incorporated--.

At Column 24, Line 34, change "flits" to --frits--.

At Column 28, Line 47, change "whcih" to --which--.

At Column 28, Line 49, change "sidechain" to --side chain--.

At Column 30, Line 37, change "slighly" to --slightly--.

At Column 30, Line 50, change "attaract" to --attract--.

At Column 30, Line 53, change "chaged" to --changed--.

At Column 30, Line 56, change "Electroosmostic" to --Electroosmotic--.

At Column 31, Line 10, change "can be be" to --can be--.

At Column 31, Line 17, change "convection new" to --convection near--.

At Column 31, Line 24, change "geometery" to --geometry--.

At Column 31, Line 31, change "pressue" to --pressure--.

At Column 32, Line 66, change "photoactivatible" to --photoactivatable--.

At Column 34, Line 22, change "fluorescese." to --fluorescence.--.

At Column 34, Line 59, change "fo" to --for--.

At Column 39, Line 24, change ""target" to --"target--.

At Column 40, Line 30, change "ce" to --α--.

At Column 40, Line 50, change "Bioconj" to --Bioconj.--.

At Column 42, Line 16, change "US98105025," to --US98/05025,--.

At Column 42, Line 54, change "r," to --$2^n$,--.

At Column 45, Line 22, change "flos" to --flows--.

At Column 45, Line 42, change "photoactivatible" to --photoactivatable--.

At Column 46, Line 33, change "postives" to --positives--.

At Column 49, Line 19, change "Malacite" to --Malachite--.

At Column 53, Line 8, change "fluorophor," to --fluorophore,--.

At Column 53, Line 19, change "optmized" to --optimized--.

At Column 53, Line 21, change "conditons" to --conditions--.

At Column 53, Line 28, change "fluorophors," to --fluorophores,--.

At Column 53, Line 46, change "09/553, 993" to --09/553,993--.

At Column 53, Line 51, change ",both" to --, both--.

At Column 55, Line 17, change "avpids" to --avoids--.

In the Claims

At Column 58, Line 19, in Claim 13, change "fluidic" to --fluidics--.

At Column 58, Line 62, in Claim 26, change "fluidic" to --fluidics--.